(12) United States Patent
Griffin

(10) Patent No.: US 11,915,140 B2
(45) Date of Patent: *Feb. 27, 2024

(54) SURGICAL ENDOSCOPE EMPLOYING MULTI-SPECTRUM RING-ILLUMINATED SURGICAL CAMERA

(71) Applicant: Cyclone Biosciences, LLC, Phoenix, AZ (US)

(72) Inventor: Stephen E. Griffin, Peoria, AZ (US)

(73) Assignee: CYCLONE BIOSCIENCES, LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/229,047

(22) Filed: Aug. 1, 2023

(65) Prior Publication Data
US 2023/0409915 A1    Dec. 21, 2023

Related U.S. Application Data

(60) Division of application No. 16/983,112, filed on Aug. 3, 2020, now Pat. No. 11,783,188, which is a continuation-in-part of application No. 16/557,074, filed on Aug. 30, 2019, now Pat. No. 10,743,756, which is a division of application No. 16/157,478, filed on Oct. 11, 2018, now Pat. No. 10,743,755, said application No. 16/983,112 is a continuation-in-part of application No. 16/157,478, filed on Oct. 11, 2018, now Pat. No. 10,743,755.

(51) Int. Cl.
| | | |
|---|---|---|
| *A61B 1/06* | (2006.01) |
| *A61B 1/00* | (2006.01) |
| *A61B 1/05* | (2006.01) |
| *G06N 3/082* | (2023.01) |
| *G02B 23/24* | (2006.01) |
| *G02B 19/00* | (2006.01) |
| *G06N 3/044* | (2023.01) |
| *A61B 1/307* | (2006.01) |
| *A61B 1/018* | (2006.01) |
| *A61B 90/00* | (2016.01) |
| *H04N 23/55* | (2023.01) |

(52) U.S. Cl.
CPC .......... *G06N 3/082* (2013.01); *A61B 1/00096* (2013.01); *A61B 1/05* (2013.01); *A61B 1/0615* (2013.01); *A61B 1/0638* (2013.01); *A61B 1/0676* (2013.01); *A61B 1/0684* (2013.01); *G02B 19/0066* (2013.01); *G02B 23/2461* (2013.01); *G06N 3/044* (2023.01); *A61B 1/018* (2013.01); *A61B 1/307* (2013.01); *A61B 90/361* (2016.02); *H04N 23/55* (2023.01)

(58) Field of Classification Search
CPC ..... A61B 1/00096; A61B 1/0057; A61B 1/05; A61B 1/0615; A61B 1/0638; A61B 1/0676
See application file for complete search history.

(56) References Cited

U.S. PATENT DOCUMENTS

2004/0073084 A1* 4/2004 Maeda ............... A61B 1/00042
600/101

* cited by examiner

*Primary Examiner* — Aaron B Fairchild
(74) *Attorney, Agent, or Firm* — Quarles & Brady LLP; Yakov S. Sidorin

(57) ABSTRACT

A surgical scope employing a multi-spectrum ring illuminated surgical camera with a ring lens and a plurality of sources of light set behind the camera and positioned radially about the longitudinal axis of the lens and/or scope.

16 Claims, 12 Drawing Sheets

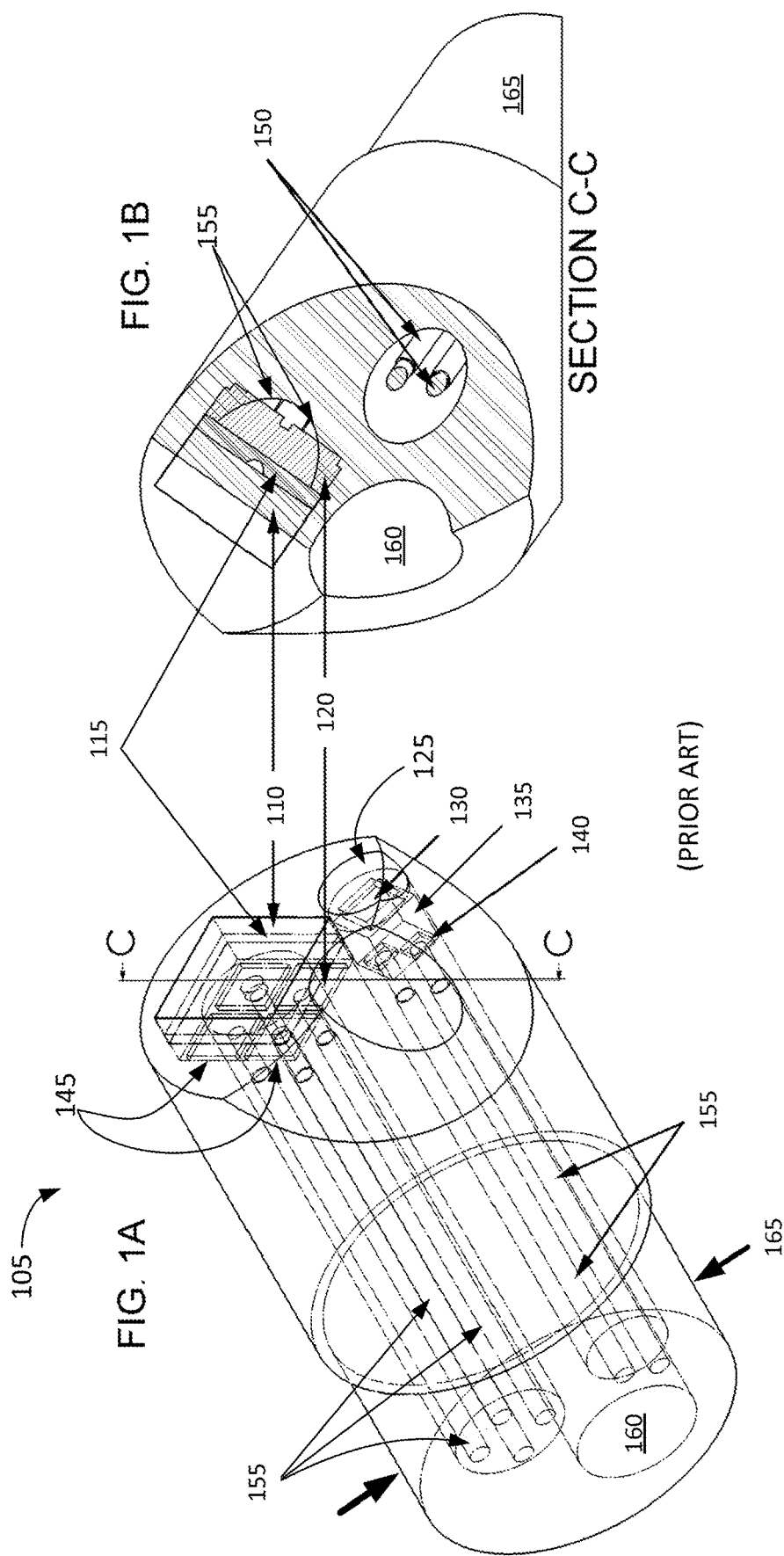

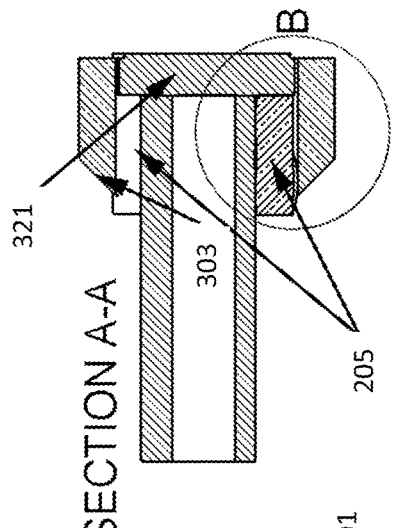
FIG. 3B
FIG. 3C
SECTION A-A
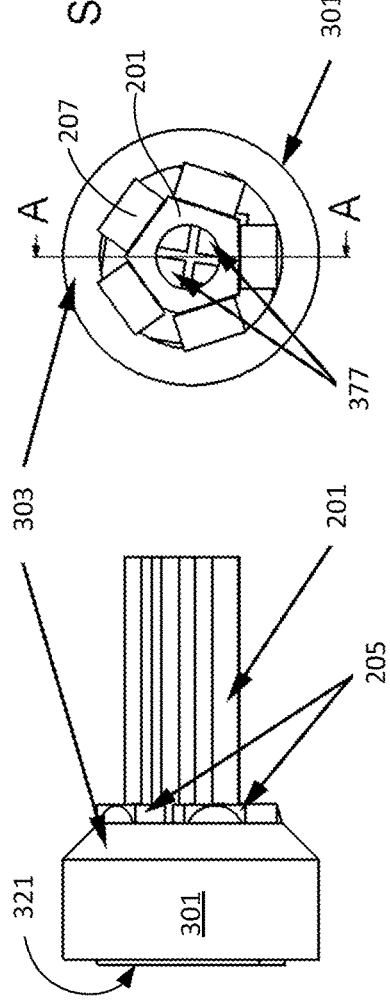
FIG. 3A
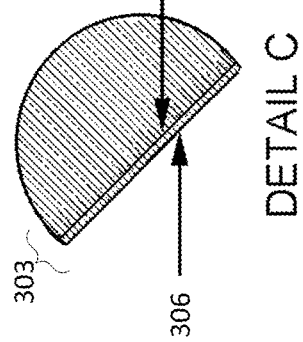
FIG. 3D
DETAIL C
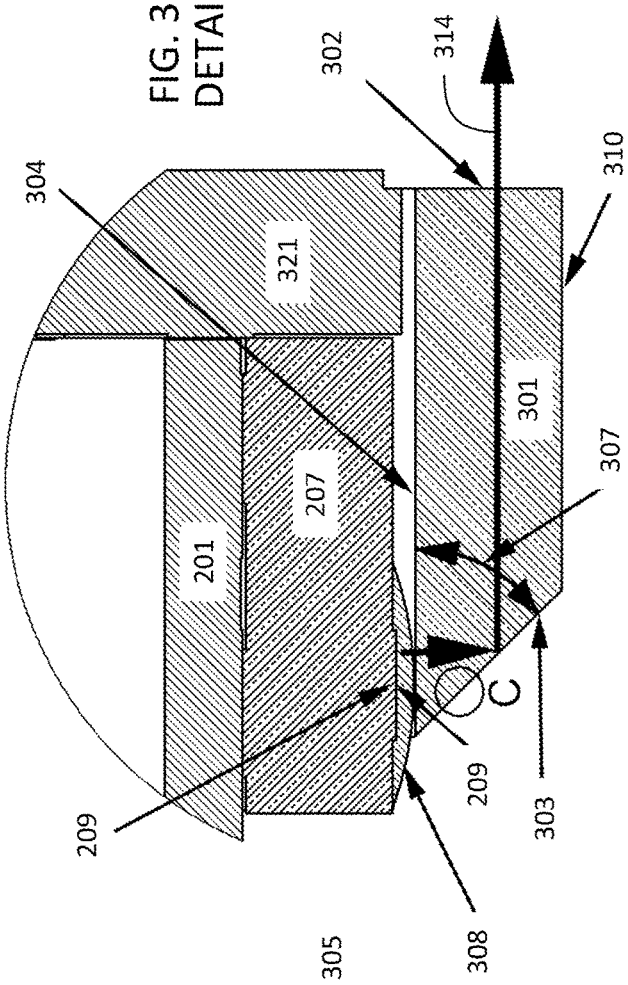
FIG. 3E
DETAIL B FIG. 4A1 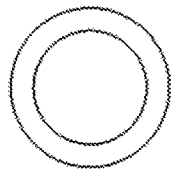 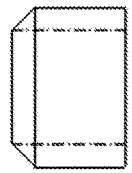 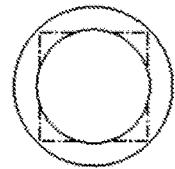 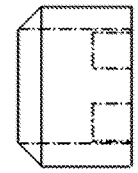
FIG. 4A2 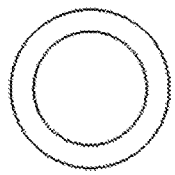 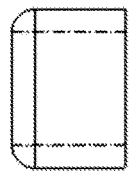 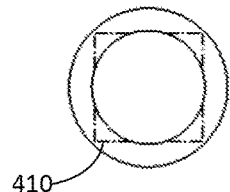 
FIG. 4B1 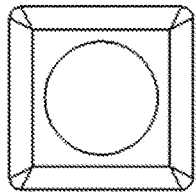  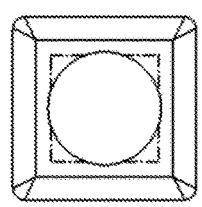 
FIG. 4C1 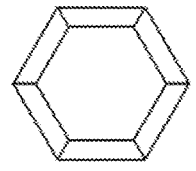  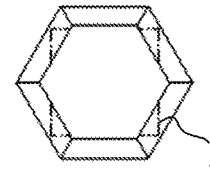 
FIG. 4C2 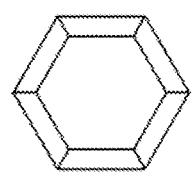  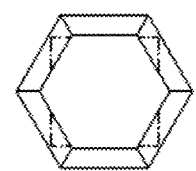 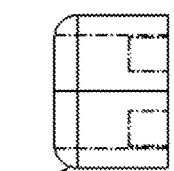
FIG. 4B2 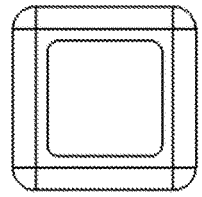 

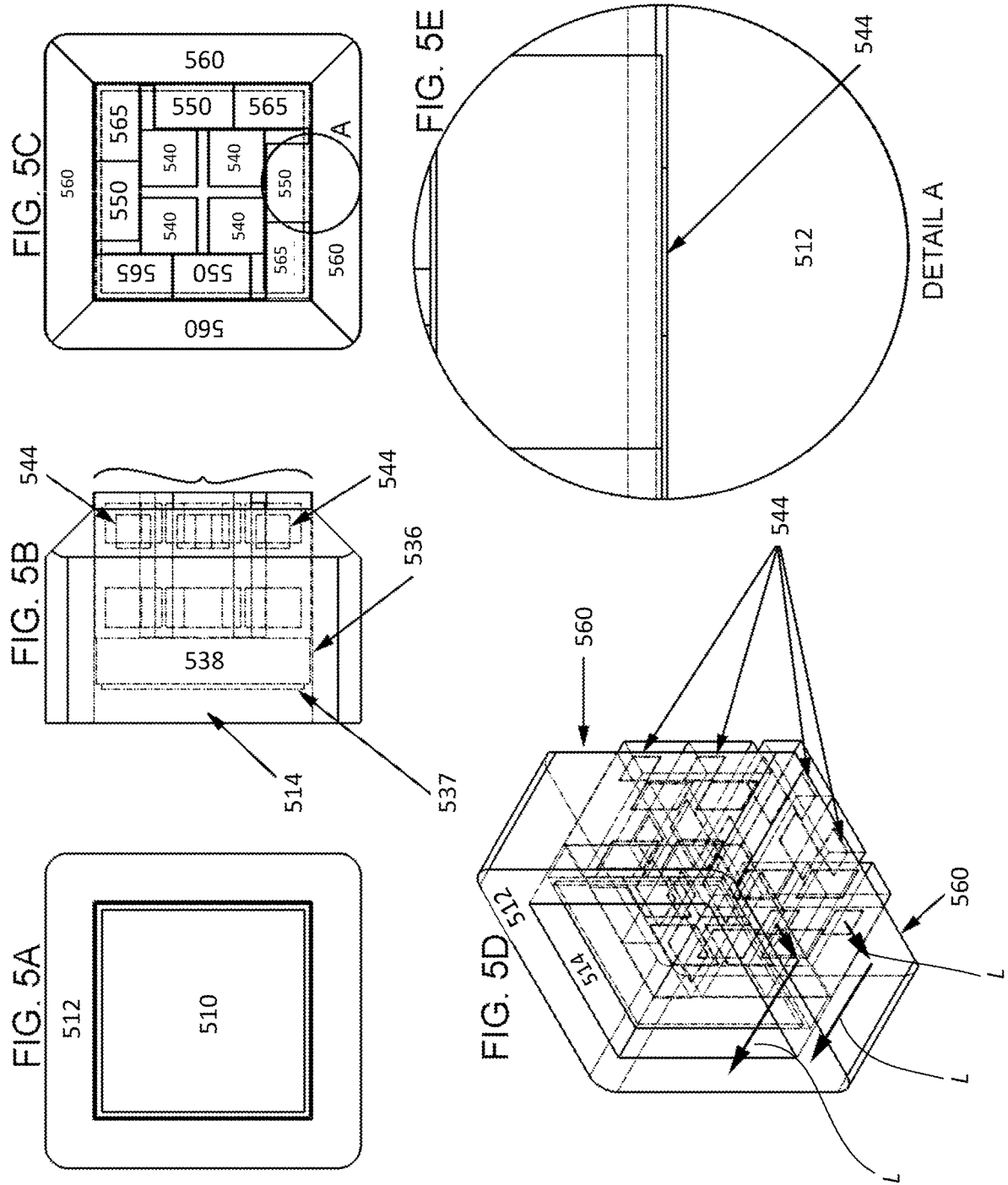

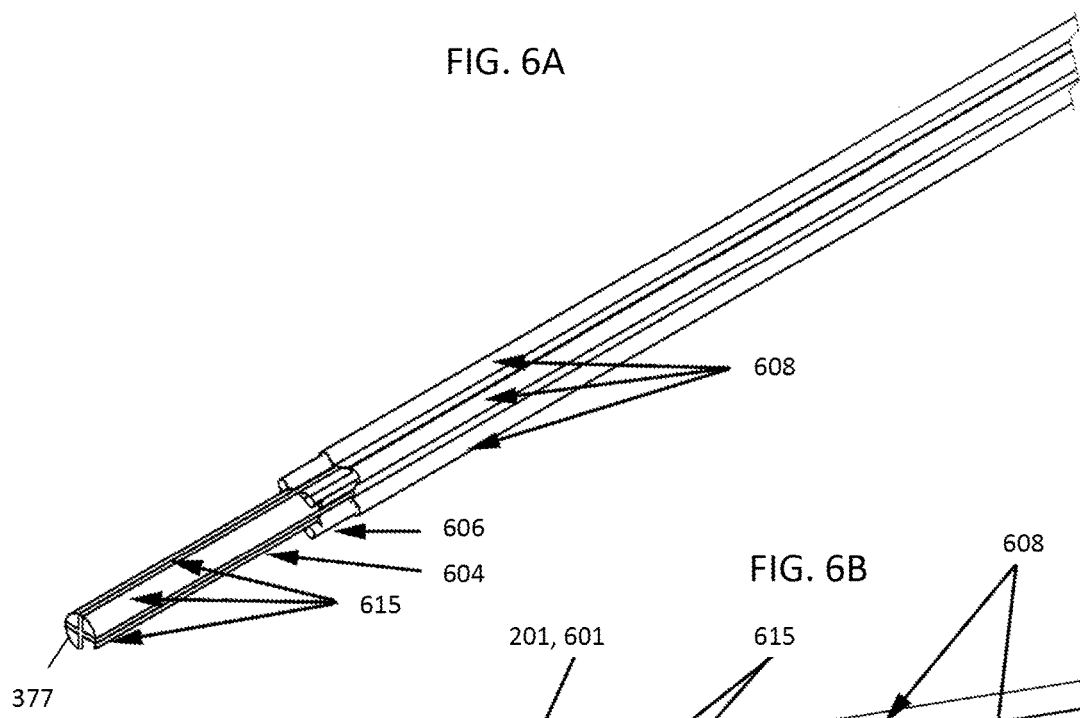
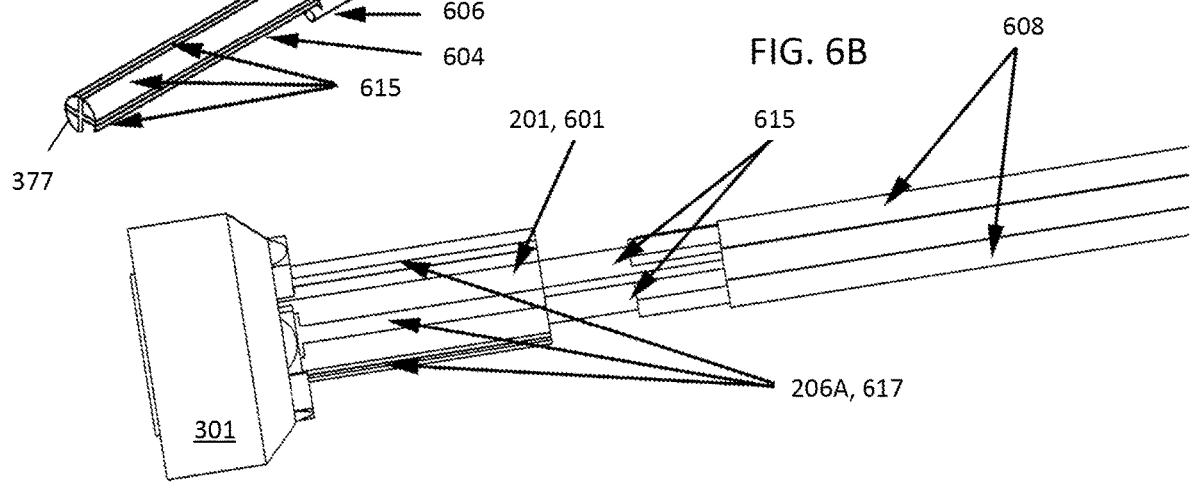
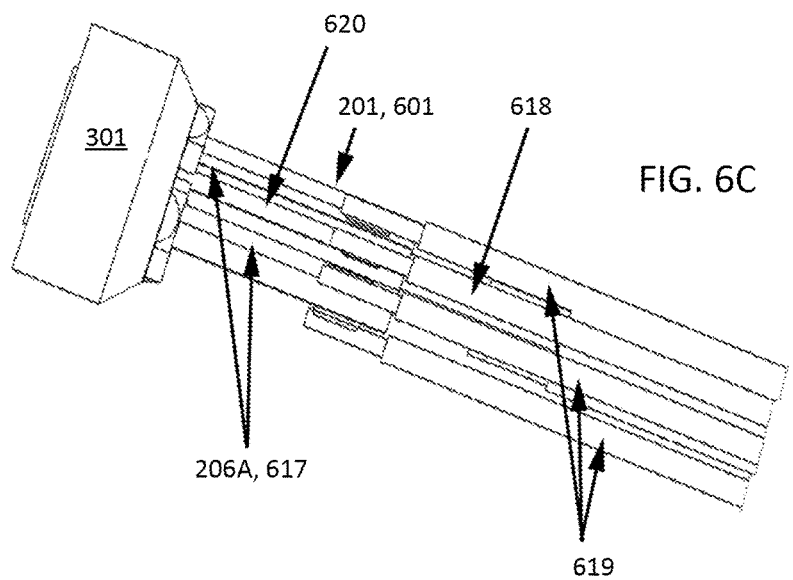

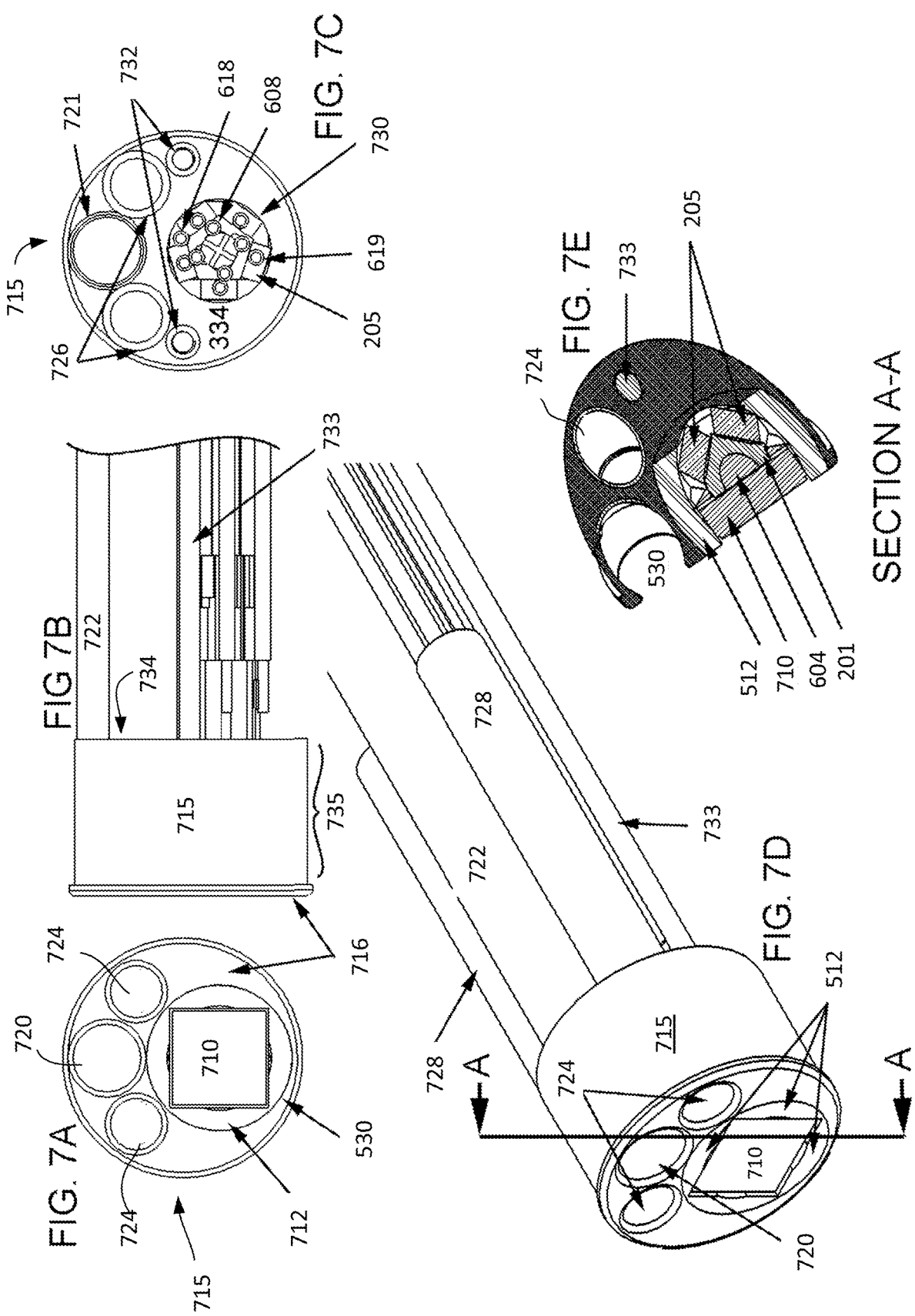

⇨ To FIG. 8F

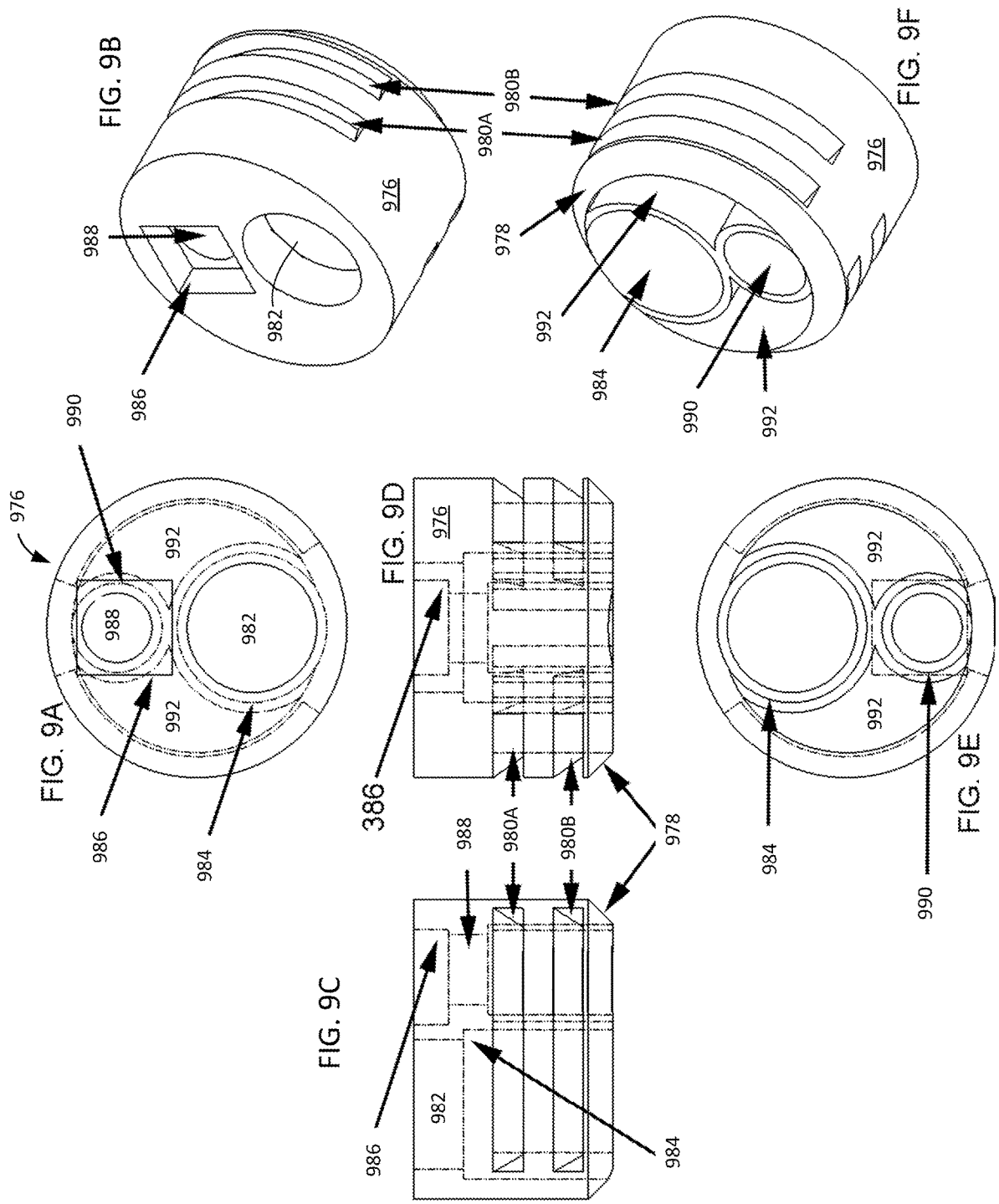

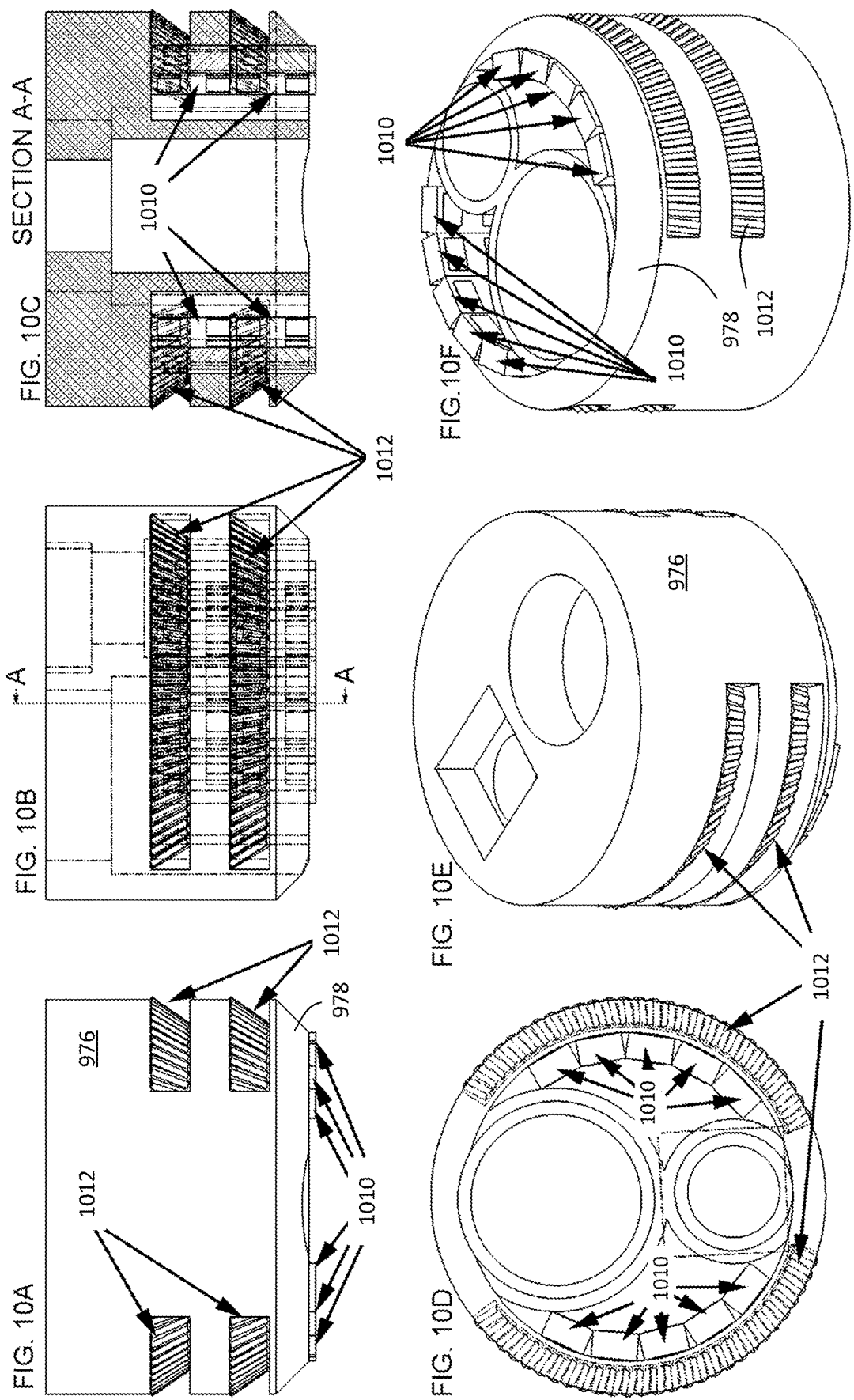

SURGICAL ENDOSCOPE EMPLOYING MULTI-SPECTRUM RING-ILLUMINATED SURGICAL CAMERA

CROSS-REFERENCE TO RELATED APPLICATIONS

This patent application is a divisional from the U.S. patent application Ser. No. 16/983,112 filed on Aug. 3, 2020 and now published as U.S. 2020/0364575, which is a continuation-in-part of the U.S. patent application Ser. No. 16/557,074 filed on Aug. 30, 2019 and now granted as U.S. Pat. No. 10,743,756, which is a division of the U.S. patent application Ser. No. 16/157,478 filed on Oct. 11, 2018 and now granted as U.S. Pat. No. 10,743,755. The U.S. patent application Ser. No. 16/983,112 is also a continuation-in-part of the U.S. patent application Ser. No. 16/157,478 filed on Oct. 11, 2018 and now granted as U.S. Pat. No. 10,743,755. The disclosure of each of the above-identified applications is incorporated herein by reference.

TECHNICAL FIELD

This invention generally relates to semiconductor imaging and/or illumination devices and, in particularly to such devices configured for use in medical catheter-based system with imaging capabilities, borescopes, and other devices for imaging inremote locations via narrow openings and channels.

RELATED ART

Adequate-quality visualization of an area of concern during exploration and treatment of internal areas of the human anatomy continues to present practical challenges. The process of visualization of the target area can be especially troublesome in minimally-invasive procedures, in which small diameter, flexible, and elongated instruments— such as catheters, endoscopes (or more specifically, ureteroscopes and duodenoscopes; —aggregately classified as surgical scopes for the purposes of this disclosure) are navigated through natural passageways of a patient/biological tissue to the target area of concern. The target area of concern may be located either in the passageway itself or in an organ that is accessible through the passageway.

A common example of the relevant procedure is provided by what is known as flexible ureteroscopy. Ureteroscopy involves actions that are used for diagnosis and treatment of urinary tract diseases (such as urinary calculi and ureteral strictures, for example). In practice, a ureteroscope is inserted through a urethral opening and threaded along the urinary tract, into the bladder, through the urethral opening, and into the kidney calyx. Diagnosis and/or treatment occur under direct visualization conventionally enabled with fiber optic coupled to imaging system(s) and/or light source(s). As known up to-date, tiny imaging cameras and light emitting diode (LED) light sources have been utilized in modern ureteroscope design. FIG. 1 depicts schematically an example of a tip portion of a modern ureteroscope 105 in two sub-FIGS. 1A, 1B.

Ureteroscopes are typically 3 mm to 4 mm (10 Fr. to 13 Fr.) in diameter 165 and include a sheath (not shown, coupled to a step on the tip 105) that encapsulates a fiber optic imaging element configured as an imaging bundle and/or imaging chip 115/120 (sensor/substrate) and wiring 155, another fiber optic illumination element configured as an illumination bundle and/or LED 130/135 (sensor/substrate) and a working channel 160. Wires are connected via contacts 140/145 (LED/sensor) located upon the substrate 135/120 (LED/sensor). Window elements 110/125 (sensor/LED) typically are employed to seal the chips from exposure to surgical irrigants during the operation of the ureteroscope.

The working channel 160 (also known as a "forceps channel") is typically dimensioned as a lumen for instrument access to tissue through the distal tip of the scope, thereby permitting passage of various devices (such as guidewires and/or optical fibers for delivery of laser energy and/or stone retrieval baskets) towards the target area. The working channel 160 can also be used for introducing sterile irrigant towards the target area. Drainage of irrigant and surgical detritus typically occurs about the outer diameter of the scope, usually housed within an "access sheath". The irrigation flow may be partially occluded by instruments present within the working channel 160, and in this case, inadequate flow may allow surgical detritus to build up and impair visualization during surgery. Accordingly, larger working channels may be preferred to both permit the employment of larger instruments in surgery and for maintenance of a clear surgical field. For reference, for a tip of a scope of related art, illustrated in FIG. 1, the total tip diameter is 3.2 mm and the working channel is 1.1 mm.

Illumination of the target area is typically provided via an optical fiber bundle that is terminated within the distal tip of the scope and that, in operation, transmits light from a light source outside of the bodily tissue. Quite recently, the users started to employ LEDs (indicated here as 130, 135) in the ureteroscope to replace the illumination fiber bundle(s). Visualization is afforded via an imaging optical fiber bundle or via a camera chip 115/120 (sensor/substrate) at the distal tip of the device 105. Most ureteroscopes also incorporate a steering mechanism (not shown in FIG. 1), which allows the distal tip of the scope to be deflected in one or more planes to follow the natural lumen with minimal trauma.

Size is of primary importance for minimally invasive imaging and access devices. Devices of larger diameters are typically less flexible (and, as a result, less "steerable"), often cannot pass smaller lumen (which is of common use in, for example, pediatrics), and induce more trauma to the tissue than smaller devices, while themselves suffering damage in forced passage through the lumen. At the same time, however, the use of larger devices offers competitive operational advantages over the use of smaller-sized devices, including that of permitting larger working channels that provide better irrigant flow and access for larger instruments. Notwithstanding, the practice shows that smaller, more flexible devices are clearly favored.

Another compromise made in imaging scopes of related art is the amount and quality of the lighting (illumination) provided to the target area. Fiber optic bundles for lighting or illumination are kept small (as far as the overall cross-sectional dimension is concerned), and utilize very small-core and uncoated optical fibers, about 20 micrometers in diameter, to minimize both the stiffness and the overall cross-sectional dimension(s) of the ureteroscope. Typically, a single fiber bundle or LED 130, 135 is used, which is positioned at or on one side of the imaging element, thereby forming a substantially spatially-uneven illumination of the visual field, particularly in a case where such visual field has complicated topography.

There remains a practical need, therefore, in a small diameter, flexible ureteroscope or duodenoscope or a similar device that is characterized by superior configuration of illumination and visualization system(s) within as compact a package as possible.

SUMMARY

Embodiments of the invention provide a surgical endoscope that includes a tubular endoscopic sheath (which, depending on the implementation, may be made of a somewhat flexible material and/or from metal) that is dimensioned to be accommodated in a bodily vessel or cavity and that encloses at least in part an endoscopic tip located at a distal end of said sheath. The endoscopic tip contains a ring lens that is configured as a unitary piece and that has a proximal end facing the sheath, a distal end, a reflecting surface at the proximal end, an emission surface at the distal end, and a longitudinal axis running from the proximal end to the distal end. The endoscopic tip also houses a) a support post extending longitudinally through the ring lens; b) multiple LED sources carried on such support post and configured to emit light radially with respect to the longitudinal axis into the ring lens towards the reflecting surface; and c) a grey-scale image capture sensor that is adjacent to the emission surface of the ring lens, that is substantially transverse to the longitudinal axis, and that faces an ambient medium. The support post may be structured to have longitudinal hollow extending throughout the support post, and contain a contact member passing through such longitudinal hollow and carrying electrical contact members within the longitudinal hollow (the electrical contact members being connected to the image capture sensor).

The reflecting surface of the ring lens may be dimensioned to receive the LED-light emitted radially and to reflect the so-received light along the longitudinal axis towards the emission surface. Depending on the specifics of particular implementation of the endoscope, at least one of the following conditions is satisfied: i) the multiplicity of LED sources includes at least one LED adapted to emit light at each of three to twelve different wavelengths; ii) the multiplicity of LED sources includes at least two LEDs adapted to emit light at each of three to twelve different wavelengths; iii) the multiplicity of LED sources includes at least one white-light LED; and iv) the multiplicity of LED sources includes multiple single-color LEDs configured such that a color of light emitted by a first single-color LED in operation is different from a color of light emitted by a second single-color LED. The support post may have multiple outer longitudinal facets extended along the longitudinal axis and a polygonal outer cross-section defined across the longitudinal axis, such that each of the outer longitudinal facets carries a corresponding LED source from the multiplicity of LED sources. In at least one embodiment the gray-scale image capture sensor may be recessed into the ring lens such that a portion of the emission surface of the ring lens remains exposed to the ambient medium and/or the endoscope includes an optical window element covering and fluidly sealing the image capture sensor in the recess of the ring lens.

Alternatively or in addition, in at least one embodiment the endoscopic tip may include at least one working channel that is longitudinally extended through the endoscopic tip and that is dimensioned to accommodate at least one of instrument access and fluid flow from the sheath to a proximal surface of the endoscopic tip. Further, such working channel and/or the ring lens may be configured to be asymmetric about a center of a proximal surface of the tip. In at least one of the implementations, the endoscope may be configured such that at least one of the following conditions is satisfied: a) the ring lens has at least one of a polygonal outer perimeter and a polygonal inner perimeter as seen in a cross-section of the ring lens defined in a plane transverse to the longitudinal axis; b) the reflecting surface of the ring lens is a substantially conical surface; c) the emission surface of the lens is a substantially planar surface transverse to the longitudinal axis; d) the sheath includes a metallic tubular member; and e) an external surface of the ring lens carries a reflective coating thereon.

Embodiments of the invention also provide a surgical scope containing an illumination system that forms, in operation, a ring-shaped distribution of illumination light and including and endoscopic tip and an endoscopic cannula (defined as an endoscopic sheath made of metal) affixed to the endoscopic tip. A plurality of guidewires adapted to affect the orientation of the endoscopic tip is passed through the cannula, while the endoscopic tip includes a ring-illuminated surgical imaging camera containing a ring-shaped lens (having a reflector at a proximal end of such lens and an emission surface at a distal end of the lens, and a longitudinal axis running from the proximal end to the distal end) and a plurality of LEDs that are adjacent to an internal surface of the ring-shaped lens and that are positioned to radially transmit light into the ring-shaped lens. The reflector at the proximal end of the lens is adapted to reflect the LED light longitudinally, along the longitudinal axis. The plurality of LEDs is defined to emit light at a three to twelve different wavelengths. (The emission of light of the plurality of available LEDs includes spatially separate emissions at each of such different wavelengths as well as the emission at the plurality of wavelengths from the same light source.) The endoscopic tip also contains a grey-scale image capture sensor recessed into the ring-shaped lens; such image capture sensor is in electrical contact with an array contact post, which post extends longitudinally through the ring-shaped lens.

BRIEF DESCRIPTION OF THE DRAWINGS

For a more complete understanding of the disclosure, reference should be made to the following detailed description and accompanying not-to-scale drawing figures, in which:

FIG. 1 presents an isometric view (FIG. 1A) and a bisected view (FIG. 1B) of an endoscopic system of related art.

FIG. 3 provides a plurality of views and expanded views of a ring illuminated surgical camera in corresponding sub-figures. Here, FIG. 3A shows a side-on view, FIG. 3B shows a head-on view, FIG. 3C shows a bisected view running along a longitudinal axis (the bisect shown in FIG. 3B as line A-A), FIG. 3E is an expanded view of Detail B shown in FIG. 3C, and FIG. 3D is an expanded view of Detail C shown in FIG. 3E.

FIG. 4 (with sub-FIGS. 4A1, 4A2, 4B1, 4B2, 4C1, and 4C2) depicts a series of ring lenses with a variety of shapes, chamfered and/or filleted geometries, and indicates recesses in such ring lenses dimensioned for carrying and/or supporting a corresponding imaging element (camera array).

FIG. 5 presents a plurality of views and expanded views of a square, ring illuminated surgical camera. Here, FIG. 5A shows an end-on view, FIG. 5B shows a transparent side view, FIG. 5C shows a rear view of the camera with the LED support removed but the LEDs remaining, FIG. 5D shows a transparent orthogonal projection depicting the path of light from the LEDs to the emission surface, and FIG. 5E shows an expanded view of Detail A in FIG. 5C.

FIG. 6 (with sub-FIGS. 6A, 6B, and 6C) illustrates certain steps of the process of assembly of a ring-illuminated surgical camera and electrically conducting leads employed by the camera. Here, FIG. 6A shows the contact post and camera leads carried thereon, FIG. 6B depicts the contact-post 604 (with the camera leads) fitted into the LED support post (which is carrying LED sources and an embodiment of the ring lens), and FIG. 6C shows the LED contacts disposed on and connected to the LED support post.

FIG. 7 presents a plurality of views of a ring illuminated surgical camera incorporated into an endoscopic device. Here, FIG. 7A shows an end-on view of the endoscopic device's tip with working channels; FIG. 7B shows a side view of the endoscopic tip; FIG. 7C shows a rear view of the endoscopic tip with guide wire contact posts and electrical leads; FIG. 7D shows an orthogonal projection of the endoscopic tip; and FIG. 7E shows a bisected, off-axis view of the endoscopic tip (the bisection is illustrated in FIG. 7D by the line A-A).

FIG. 9 illustrates a plurality of views of a related embodiment of a ring lens configured as a single-piece (one-piece) unit with working-channels formed in it and for use in a ring-illuminated surgical camera. Here, FIG. 9A shows an end-on view, FIG. 9C shows a first side view, FIG. 9D shows a second side view, FIG. 9E shows a rear view of the working-channel ring lens. FIG. 9B shows an orthogonal front projection and FIG. 9F shows an orthogonal rear projection of the working-channel ring lens.

FIG. 10 presents a plurality of views of a related embodiment of a working-channel ring lens, of the surgical endoscope, which lens is configured for use in a ring-illuminated surgical camera. Here, FIG. 10A shows a side view of the ring lens, FIG. 10B shows a transparent side view of the ring lens, FIG. 10C shows a bisected view of the ring lens (the bisection is indicated in FIG. 10B with the line A-A), FIG. 10D shows an rear view of the ring lens carrying LEDs, FIG. 10E shows a top-down orthogonal view of the ring lens, and FIG. 10F shows a bottom-up orthogonal view of the ring lens carrying LEDs.

Figure 2A:
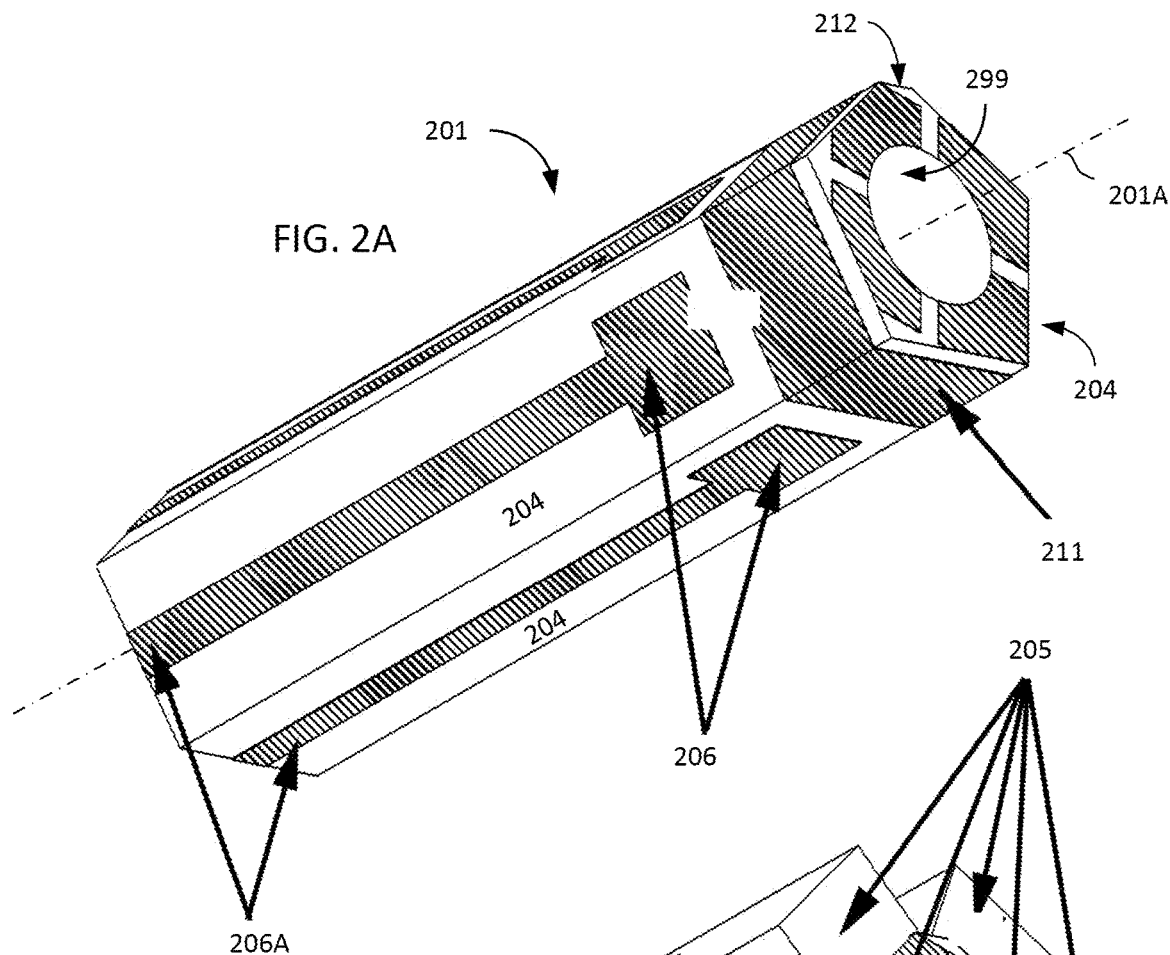
FIG. 2 shows a LED stack with exposed electrodes (FIG. 2A, the LED support) and with affixed LEDs (FIG. 2B).

In the Drawings, generally, like elements and/or components may be referred to by like numerals and/or other identifiers; not all elements and/or components shown in one Drawing may be necessarily depicted in another for simplicity of illustrations. The specific embodiments are illustrated in the drawings are intended to be illustrative and not limiting the scope of the invention.

DETAILED DESCRIPTION

The following disclosure addresses some constituent components of and configuration(s) of a surgical scope designed to provide illumination of the target field with the ring-like (substantially annular) or circular spatial distribution of light, thereby allowing the user of the scope to clearly image and/or visualize the target field. The components and structure of the scope include a Ring-Illuminated Surgical Camera (which may be referred to herein as RISC) that features at least one light emitting diode, a ring lens, and an electronic imaging sensor. Importantly, the spatial cooperation of the sources of light (as discussed in provided examples—LEDs), the ring lens, and the imaging sensor in an embodiment of the RISC is judiciously configured to decrease the cross-sectional diameter of a surgical scope while, at the same time, providing improved diagnostic of surgical capabilities.

In one embodiment of an RISC, one or more LEDs are positioned behind, rather than in plane with, an electronic imaging sensor. (In this disclosure, the terms "electronic imaging sensor", "camera", and "camera array" are used to define an electronic device that is adapted for the conversion of light to electrical signals, which signals can be converted back to an image. Examples of such electronic devices include CMOS sensors and CCD sensors.) Notably, in substantially any implementation of the ring-illuminated surgical camera and the endoscope, the grey-scale image capture sensor is configured to include a plurality of pixels each having a extent of less than about a few microns (4 or 3 or 2 or even 1 More preferably, the grey-scale image capture sensor has dimensions of less than 2×2 mm (length× width), less than 1.5×1.5 mm, less than 1×1 mm, less than 0.75×0.75 mm, or less than 0.5×0.5 mm. In still another instance, the grey-scale image capture sensor carries greater than about 50,000 pixels (50 kilopixels or 50 kP), 100 kP, 150 kP, 200 kP, 250 kP, or even 300 kP.

Figure 2B:
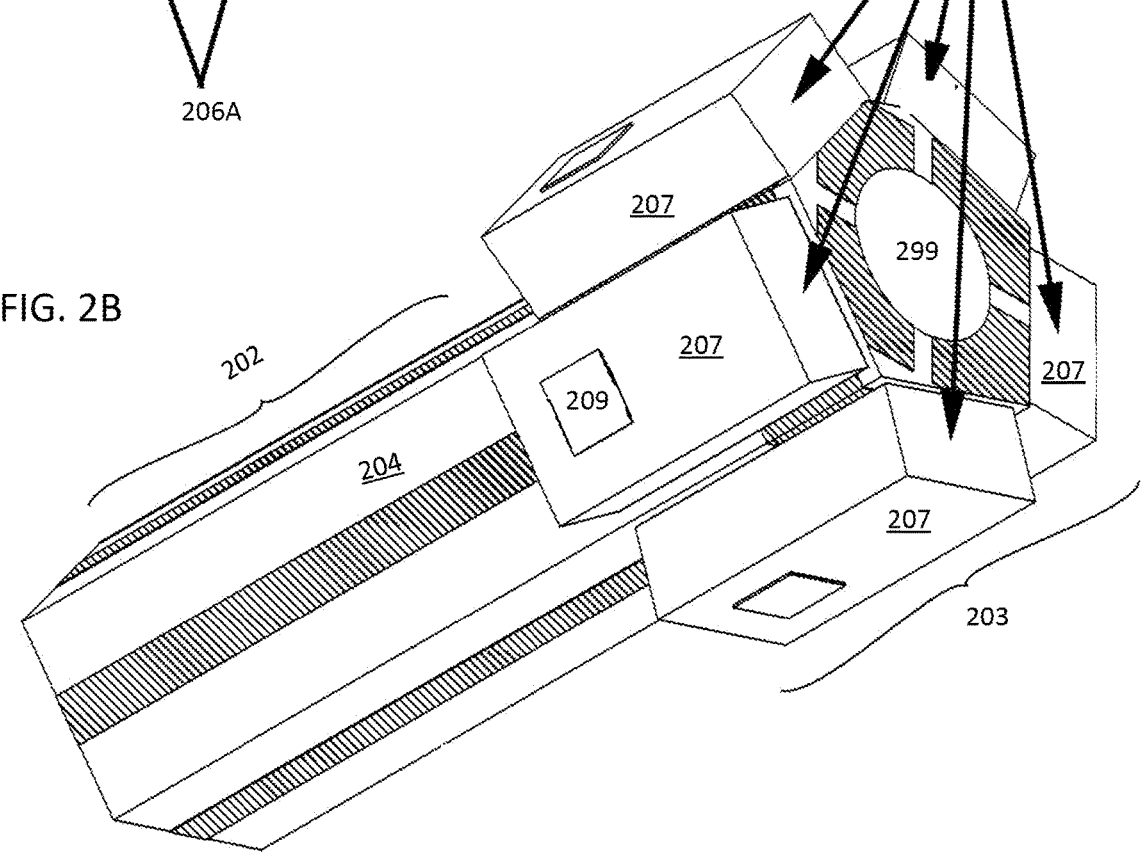

To this end, FIG. 2 (and sub-FIGS. 2A and 2B) illustrates a stack (a compact arrangement of) a plurality of LED-based light sources 205 affixed to an LED support (LED support post) 201. Each of the LED-based light sources 205 includes a corresponding LED emitter 209 disposed upon a corresponding substrate 207 and positioned behind and in a nonparallel fashion with respect to an electronic imaging sensor (not shown). The LED support 201 (FIG. 2A) has a plurality of support faces or facets 204, each carrying at least one LED power electrical contact layer 206 (and/or LED lead 206A) and a portion of a common return electrical contact or ground 211. The common LED ground 211 can be deposited across a plurality of support faces 204 and—as shown—forms a continuous band or stripe of an electrically conducting material circumscribing the support 201 in a plane transverse to the axis 201A of the support 201.

The LED support 201 is structured to have multiple support facets 204—as non-limiting examples, 3, 4, 5, 6, 7, 8, 9, or 10 support facets—and is dimensioned according to the number of such support facets to have a respectively corresponding triangular, square, pentagonal, hexagonal, heptagonal, octagonal, nonagonal, or decagonal cross-section. While the use of additional support faces can be contemplated (in excess of for example), the LED support 201 is preferably kept sufficiently dimensionally narrow to enable its efficient use in practical surgical scopes. For example, in one implementation the LED support with LEDs mounted on it is of cross-sectional dimension that is equal to or less than the sensor chip of the camera array used in the particular embodiment. The facets 204 of the support 201 are approximately equal in width to the LED substrates 207 that are about 0.350 mm wide while the support facet may be about mm wide. Preferably, the LED support 201 has a square, pentagonal, or hexagonal cross-section (that is, the LED support 201 preferably has 4, 5, or 6 support faces 204; as shown—5 support faces). Each support face, preferably, further includes at least one LED contact 206 electrically connected to an LED electrical lead 206A and a portion of the LED return/common/ground or common LED ground 211.

In certain instances—and as shown in FIGS. 2A, 2B—the LED support 201 can be structured to have, in addition to a plurality of support faces 204, an LED ground face 212 extended along the axis 201A. The LED ground face 212 can be dimensioned to be substantially congruent with a given support face 204 or, alternatively, be narrower than a given support face 204 (whereas the length of the ground face 212 along the axis 201A is preferably the same as those of the support faces 204). For example, FIG. 2A illustrates the LED support 201 with five (5) common faces 204 and a narrower LED ground face 212, arranged to form a post 201 with a cross-section having a dimensionally-irregular hexagon as a perimeter. When the LED support 201 includes the LED ground face 212, the common LED ground 211 is preferably carried across each of the support faces 104 and the LED ground face 212 (e.g., the layer 211 is wrapped around the LED support 101). In a common instance, the LED contact 206, the LED lead 206A, and the common LED ground 211 layers include an electrically-conducting metal, preferably copper, silver, or gold.

The LED support 201 preferably carries at least one LED source 205 on each of the support faces 204. The corresponding LED emitters (or chips or dies) 209 commonly have flat or planar surfaces and are configured to emit light transversely or even perpendicularly to these planar surfaces (which transverse direction is defined as a local primary emission direction, or direction of primary emission). Preferably, this primary emission direction is not parallel to the longitudinal axis 201A. More preferably, a given LED substrate 207 (herein defined by its planar surface) is substantially parallel to the support face 204 upon which the LED source 205 is affixed. Each LED source 205 is preferably affixed (e.g., soldered) to a corresponding LED contact 206 and the LED ground 211.

In a related and non-exclusive case, the LED support 201 may be structured to include a proximal region 202 and a distal region 203. In this case, the LED sources 205 are carried on (affixed to) the distal region 203 with the LED leads 206A extending to the proximal region 202. The distal region 203 preferably includes at least portions of the LED contacts 206 and the common LED ground 211.

The LED support 201 may be configured to include a bore or pathway or hollow 299 through such support from the proximal end to the distal end, dimensioned to accommodate therein an imaging contact post 604 (discussed later in reference to FIG. 6) preferably without contacting the LED electrical contact and/or leads.

FIG. 3 (including sub-FIGS. 3A, 3B, 3C, 3D, and 3E) illustrates some structural details of the camera portion of the surgical endoscope of the invention. Here, FIG. 3A shows a side-on view of the camera portion including the assembly of the LED support post 201 carrying LED sources 205 encased in the ring lens 301 and a portion of the camera array (image sensor) 321 protruding from inside the lens 301. FIG. 3B shows a head-on view of the same portion with the camera array removed but showing electrical contact pads 377 for the camera array. FIG. 3C schematically illustrates a bisected view of the embodiment of FIG. 3A running along a longitudinal axis (the bisection line is indicated in FIG. 3B as A-A).

In an expanded view if Detail B (of FIG. 3C) that is shown in FIG. 3E, one case see that each LED source 205 can further be equipped with an LED-radiation-shaping lens (or, an LED lens, for short) 308 carried on or at least partially covering a given LED emitter substrate 207 and the facet of the LED emitter 209.

(The skilled artisan will appreciate that, since the LED lens 308 is placed adjacently to the internal surface of the ring lens 301, the LED lens 308 and the ring lens 301 are preferably structured in a mutually-dependent relationship. Specifically, the LED lens is configured to have an external surface that is dimensionally matched to (or substantially congruent with) the internal surface of the ring lens 301. In one non-limiting instance, the LED lens 308 is structured to have a semi-cylindrical surface with a curvature that is matched to the curvature of the internal surface of the ring lens 301. In another instance, the LED lens 308 can have a flat or plurality of flat surfaces that substantially geometrically-match to a plurality of flat internal surfaces of the ring lens 301. In yet another non-limiting instance, the LED lens 308 can have a pre-determined shape and the internal surface of the ring lens 301 can be matched (cut or formed) to match that shape of the external surface of the LED lens 308.

It is appreciated, therefore, that the radiation-shaping lens 308 is dimensioned to direct light (radiative emission) from the LED emitter 209 into a ring lens 301 disposed about the LED support 201 and the LED sources 205. As shown in the cross-sectional view of FIG. 3E, the ring lens 301 preferably includes an internal surface 304, an external surface 310, a surface 303 configured as a reflecting surface or reflector, for short. The reflecting surface 303 as shown is dimensioned to be a substantially conical surface—considering the substantial axially-rotational symmetry of it about the axis of the ring lens 301—and, therefore, perceived as a straight line in a cross-section containing a longitudinal axis of the ring lens 301), per FIG. 3E. The ring lens 301 also includes an emission surface 302, shown in this example to be a substantially planar surface that is transverse to the longitudinal axis of the ring lens, and facing the ambient medium at the distal end of the overall scope instrument.

In one implementation, the ring lens 301 has a radial thickness (measured with respect to the longitudinal axis of the ring lens) that is substantially constant as a function of a coordinate chosen on the ring lens along such longitudinal axis. (In a related implementation, the so-defined thickness of the lens may vary along the longitudinal axis of the lens 301). As depicted in FIG. 3E, light from the LED source 205 (illustrated by large arrows 314) is directed from the facet of the emitter 209, through the radiation-shaping lens 308, and into the ring lens 301 as a result of transmission through the internal surface 304 of the rig lens 301. The ring lens 301 is coordinated in space such that its judiciously shaped reflector surface 303 receives and further reflects or redirects the light from the LED emitter 209 through the body of the lens 301 substantially along the longitudinal axis of the ring lens to and out of the ring lens emission surface 302. (It is understood, therefore, that as a result of specific coordination of the constituent components of an embodiment of the invention, the plurality of light emitters 209 are located adjacently to the internal surface 304 of the ring lens. In one instance, the RISC includes 4 to 8 LEDs, in another instance, the RISC includes at least one LED for each common face on the LED support (see the discussion of FIG. 2A which depicts an irregular hexagonal cross-section where the LED support having five (5) common faces). In yet another instance the RISC include 3-20, 4-16, 5-15, or 6-10 LEDs.

Depending on the specifics of a particular implementation, light emitters 209 of the LED source 205 can be chosen to be substantially identical or selected to have different emission wavelengths. For example, light emitters may be chosen that generate light at at least one of the three to twelve different wavelengths selected from an absorption maxima of a surgical chromophore. The surgical chromophores can be selected from the absorption peaks, the bathochromic shifts, and hypochromic shifts of in vivo materials, where the in vivo materials can be selected from an endogenous chromophores, variants or degradation products thereof, and mixtures thereof. For example, wavelength may be selected to produce fluorescence in dyes with preferential uptake in cancerous tissues, or for strong absorption in subsurface blood vessels (hemoglobin), nerve bundles (melanin) or connective tissue (collagen) to permit non-invasive detection of subsurface structures.)

FIG. 3D schematically illustrates a specific version of configuration of the reflector 303. As shown, the reflector 303 may be configured not as a singular surface of the ring lens but rather as a complex surface element that includes an internal 305 and external 306 components (or surfaces).

Generally, the reflector 303 is formed to be inclined relative to the internal surface 304 (or relative to the longitudinal axis of the LED support 201) at an angle 307 (the value of which may range from about 35° to about 55°). In one instance, the reflector 303 is judiciously inclined to ensure the total internal reflectance (TIR) of light incident (internally to the lens 301) onto the surface 303 from the LED emitter 209, towards the emission surface 302. In a related case, the reflector 303 (specifically, the external component 306), the ring lens internal surface 304, and the ring lens external surface 308 can be coated with a high-reflectance (>95% reflectance or even >99% reflectance) coating (for example, a layer of silver) to improve the reflection and redirection of light 314 within the ring lens 301. The overall device, as discussed below, includes a plurality of LEDs, the emissions from which may be chosen to be spatially blended to produce substantially uniform illumination about a camera array 321.

As has been already understood by a skilled artisan, the ring lens 301 generally includes a ring-shaped (as seen in a cross-sectional plane transverse to the longitudinal axis of the ring lens) body; notably, while the lens 301 is a ring lens, such lens is not required to possess circular symmetry. The ring lens 301 can be substantially annular or, alternatively, polygonal in a cross-section and possess the same number of sides as the LED support (or LED support post) 201. To this end, and depending on details of a particular implementation and as illustrated in sub-figures of FIG. 4, a given ring lens 301 can be dimensioned to have various cross-sections—for example, the one that has a substantially round perimeter (see FIGS. 4A1, 4A2), a substantially square perimeter (see FIGS. 4B1, 4B2), pentagonal, or hexagonal (as in FIGS. 4C1, 4C2). In these examples, the ring lens can have a countersink or recess surface (dimensioned to accommodate the corresponding camera array/image sensor), see the examples of rectangular recesses indicated with lines 410, 414. Notably, the proximal end of the ring lens can be chamfered or filleted (see 418, 420 as examples). In one instance, the ring lens may include an external surface that is "mirrored" (coated with high-reflectance coating). In still another related example, the ring lens may contain an emissions face or facet (such as facet 302, through which the light from the LEDs exits the ring lens, as discussed in reference to FIG. 3), which may be configured as a planar surface. (In other examples, the emissions face can be convex, concave, convex conical, or concave-conical.) Notably, the selection of the orientation of the emissions facet can be dependent on the number of LEDs employed in a given camera, the divergence of radiation emanating from the LEDs and the geometry of employed camera array, and any additional tools that are used in a surgical space in conjunction with the surgical endoscope employing an embodiment of the discussed camera. In one specific implementation, the ring lens may be configured as a unitary, single-piece element made of fused silica, quartz, sapphire, crown glass, or polymeric material.

FIG. 5 (with sub-FIGS. 5A, 5B, 5C, 5E, and 5D) depicts another example of the RISC (here, nether the LED support nor the imaging contact post are illustrated for simplicity). In this example, the ring lens 512 (shown in a sub-FIG. 5A in front view) has a substantially square cross-sectional profile. Furthermore, in this example, the ring lens 512 does not include a countersink, but the inside dimension of the ring lens is approximately the same as the corresponding outer dimension of the camera array 510 (and, for example, within about 0.01, 0.02, 0.03, 0.04, 0.05, 0.06, 0.07, 0.08, 0.09, or 0.1 mm of appropriate tolerance of the outer dimension of the camera array 510).

As shown, the camera array 510 rests within the internal space (hollow, lumen) defined by the cross-section 536 of the ring lens 512 for positioning the sensors. The camera array can be set back (proximally) beneath a window/plate 514 that is configured to fluidly seal the sensor space and protect the surface of the array inside the lens 512. In another related case, the camera array can be disposed substantially flush with the emission surface of the ring lens 512. In yet another related implementation, the ring lens 512 and the window 514 can be formed as a single piece of optically transparent material (e.g. fused quartz, fused silica, sapphire, polymer, crown glass) dimensioned such that the volume for the camera array is provided within this single piece of transparent material.

As shown in FIG. 5—and in further reference to FIG. 6—the camera array 510 can be equipped with a chip 537 and a substrate 538, on the proximal side of which camera electrical contacts 540 are disposed. The camera electrical contacts 540 are preferably placed in electrical contact with the electrical contacts of the camera array itself, or traces 615 (camera leads) carried on the contact post 604 (all visible in FIGS. 6A and 6B). In one instance, the chip 537 (or chip face) is adjacent to, or in contact with the window 514.

As mentioned earlier, an embodiment of RISC can include a plurality of LEDs that can be either grouped or individually distinct—spectrally speaking, that is by wavelength or wavelength range of light such LEDs emit in operation. FIG. 5C depicts eight LEDs in two groups of four LEDs each (550 and 565). Preferably, the RISC includes at least 3, 4, 5, or 6 units of "white" light LEDs 550 that are substantially symmetrically (with respect to, e.g., an axis of the ring lens) placed about the ring lens 512. Herein, the symmetrical placement in one specific case may imply a rotational symmetry along the longitudinal axis of the lens.

Preferably, the symmetrical placement of the LEDs with respect to the axis of the ring lens 512 is configured such that, when placed and actuated, the "white" light LEDs provide illumination about the camera array to have the resulting spatial distribution of light projected on the target scene to be substantially axially symmetric. When present, the auxiliary LEDs 565 are configured to generate light in one or more spectral band of the visual portions of spectrum (that is, of specific colors).

Examples of LEDs suitable for use with an embodiment include LEDs generating blue or red light (to accentuate topography of blood vessels), UV light (to stimulate targeted fluorescent dyes), or light of different color temperatures (to provide alternative lighting or contrast when the surgical field is viewed) via the camera array 510.

FIG. 5D depicts light (denoted with large arrows L) exiting the LED emitters 544 and entering the ring lens 512 upon reflection with the tilted mirrored surface 560 (or as a result of the TIR off of the not-mirrored surface 560), and then exiting the lens 512 about the camera array/imaging sensor 510, as was discussed in reference to FIG. 3E. In contradistinction with embodiments of related art, however the proposed configurations provide several-fold more light in the surgical field and the delivered light is far more uniformly distributed about the imaging element while requiring less space within the endoscope tip than other arrangements.

Referring now to FIG. 6 (with sub-FIGS. 6A, 6B, and 6C) and in further reference to FIG. 3, FIG. 6A illustrates schematically a portion of the surgical endoscope of the invention. As shown, this portion includes the contact post 604 carrying the electrical traces 615 on the side surface of the contact post 604 and electrical contacts or pads 377 configured to establish electrical contact with the image sensor (camera array, 510 for example), as well as camera conductors 608 (which are in electrical contact with the traces 615 and are preferably affixed or even soldered—606—to the traces 615). The conductors 608 can be configured as standard electrical wires or as a bundle of insulated individual wires fitted about at least a portion of the contact post 604, or as a coaxial shielded cable. The LED support post (201, 601) is shown in FIG. 6B to carry the ring lens 301 and the LED electrical contacts or leads 206A, 617 and with the distal portion of the contact post 604 inserted into the hollow 299 of the LED support post (201, 601), preferably with a minimum gap of about 0.1 mm, 0.2 mm, 0.3 mm, 0.4 mm, 0.5 mm, 0.6 mm, 0.7 mm, 0.8 mm, 0.9 mm, or 1 mm between the proximal end of the LED support 201 and the ends of the camera conductors 608—depending on specifics of a particular implementation.

Another aspect of the discussed configuration includes wiring for the LED sources 205. As shown in FIG. 6C, for example, an LED conductor 619 is preferably in electrical contact with (more preferably affixed to, even more preferably soldered to) an LED lead 617 (shown as 206A in FIG. 2A). In one example, there is one respectively-corresponding LED conductor for each of the LED sources 205; in another example, there is wiring configured such that the LED sources 205 are connected in series or in parallel. In either example, a complete circuit requires a ground (return). Preferably, a common conductor 618 is disposed in electrical contact with, more preferably affixed to, even more preferably soldered to the common LED ground 620 (shown as 211 in FIG. 2A). In another instance, each LED 205 (FIG. 2) can be in electrical contact with a ground, or a plurality of LED sources 205 can be in electrical contact with a single ground. Preferably, there is one LED conductor 619 for each LED/camera lead 617, thereby providing a means for individually and selectively activating (actuating/illuminating) each of the LED with which the embodiment of the camera is equipped. (A proximal end-on view of the arrangement of the LED sources 205, LED conductors 619, the common conductor 618, and the camera conductors 608 is depicted in FIG. 7C as discussed below.)

An embodiment of the surgical scope, therefore, may include the ring-illuminated surgical camera with camera contract post 604 and the camera array 510, with the leads and grounds carried by the LED support 201 and the contact post 604, as well as the LED conductors 619, the common conductor 618, and the camera conductors 608 each in electrical contact with the LEDs, leads, grounds, or camera array. Alternatively, the embodiment can include a light-source configured to provide a substantially circumferential illumination of the desired target, and feature the LEDs 205 and the LED support 201 (as shown in FIG. 2) and a camera component that includes the camera array 510 and the contact post 604.

Certain features and elements of the working (distal) end of an embodiment of the endoscope, which incorporates an embodiment of RISC, are illustrated in FIG. 7 (with sub-FIGS. 7A, 7B, 7C, 7D, and 7E). In one example, the tip 715 of the endoscope body that has a tip face 716, which includes at least one counter bore recess dimensioned for mounting an embodiment of the RISC therein. The tip 715 can further contain a working channel/port 720 and a counter bore 721 configured for mating the working channel liner 722, an auxiliary channel/port 724, and a counterbore 726 dimensioned for mating with a conduit 728. (The conduit 728 may be configured, for example, for use in continuous flow irrigation or other needs). The tip 715 further accommodates a RISC bore 730 for mounting the RISC assembly as depicted in FIG. 3; and a turned down region 735 having an exterior diameter for mating with an endoscopic outer sleeve/sheath/cannula (not shown).

In the embodiment of FIG. 7, the ring lens 712 is mounted within the tip 715 of the scope body. The camera array 710 is shown to be shaped substantially squarely (due to the 2-dimensional grid design of the detecting elements; but other spatial shapes can be imagined). FIGS. 7A and 7D depict a squarely-shaped, camera countersink 710 in the ring lens 712 dimensioned to receive the camera array 710 that, therefore, is counter sunk into the ring lens 712. As a result—and in comparison with the embodiment of FIG. 3C—the face of the camera array 710 is shown positioned substantially flush with the emission surface of the ring lens 712. (In another instance, the face of the camera array can extend beyond the emission surface of the ring lens. In one example, the camera array may be disposed to seat on the ring lens, while in a related implementation the camera array may be disposed within the internal diameter of the ring lens.)

The tip 715 of the embodiment of the surgical scope of the invention can further be configured to accommodate steering wires 733—shown in FIGS. 7B, 7D, 7E—used to control the orientation of the face 716 of the tip 715 with respect to the axis of the body of the scope. Such steering wires 733 can be mounted within receiving longitudinal holes or passages 732, that form the opening(s) at the proximal surface 734 of the scope tip body 315. To this end, FIG. 7A shows an end-on view of the tip 715, whereas FIG. 7C shows an internal view of the scope tip body 715 as seen from the other, proximal end of the scope.

In one implementation, however, the steering wires are mounted to the tip body 715 within the receiving holes 732.

FIG. 7E illustrates a diagonal cross-section of the scope tip body 715 depicted in FIG. 7D and formed along the plane marked A-A. in this cross-section, portions of the LED support 201, LED sources 205, and sensor contact post 604 are visible. Other elements pf the scope described in FIGS. 3, 6 may be seen in the embodiment of FIG. 7C as well, for orientation: sensor conductors 608, LED power conducting member 619, and common/return conductors 618.

Figure 8A:
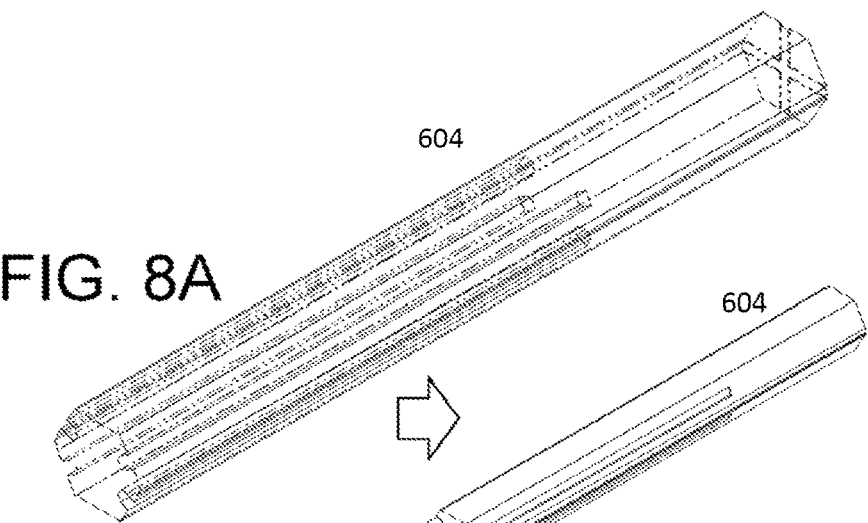
FIG. 8 provides illustrations to a sequence of steps of construction of a ring-illuminated surgical camera in corresponding sub-figures, starting from the camera contact post in FIG. 8A, to the addition of camera leads in FIG. 8B, and to the addition of the LED support in FIG. 8C. This is followed by the addition of a first LED in FIG. 8D, auxiliary LEDs in FIG. 8E, and then the addition of LED leads in FIG. 8F, the addition of a camera in FIG. 8G, and the addition of a ring lens in FIG. 8H.
FIG. 8I presents a transparent orthogonal projection of the ring-illuminated surgical camera.
Figure 8B:
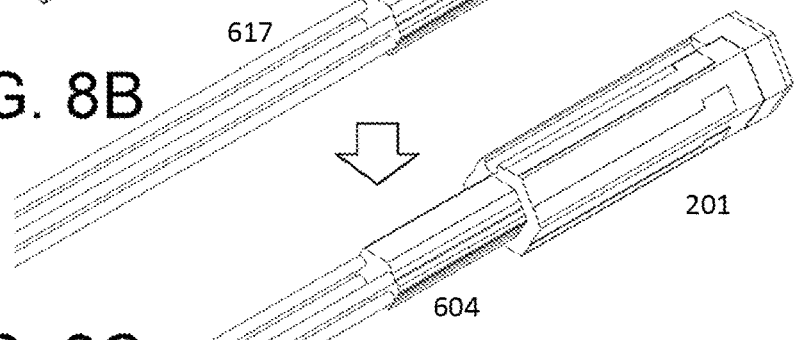
Figure 8C:
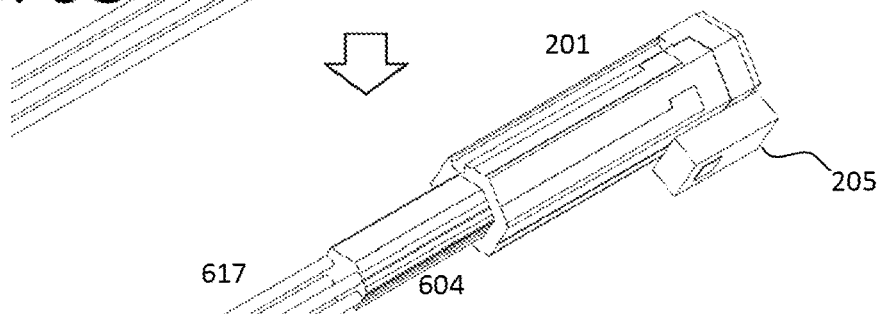
Figure 8D:
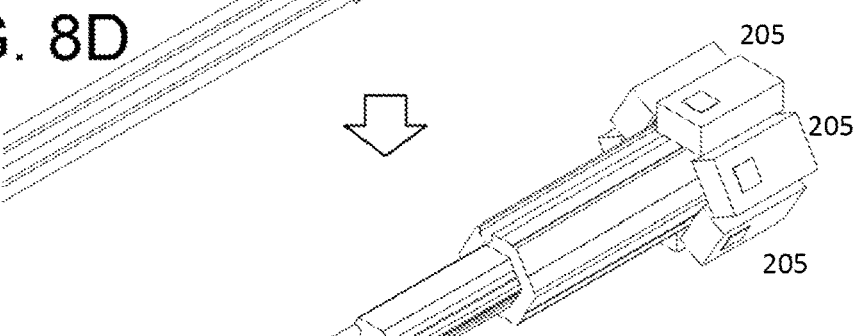
Figure 8E:
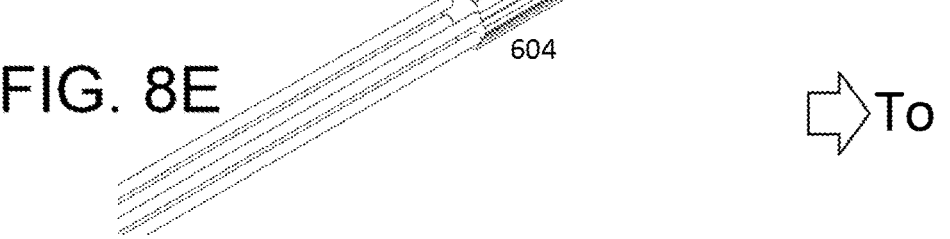
Figure 8I:
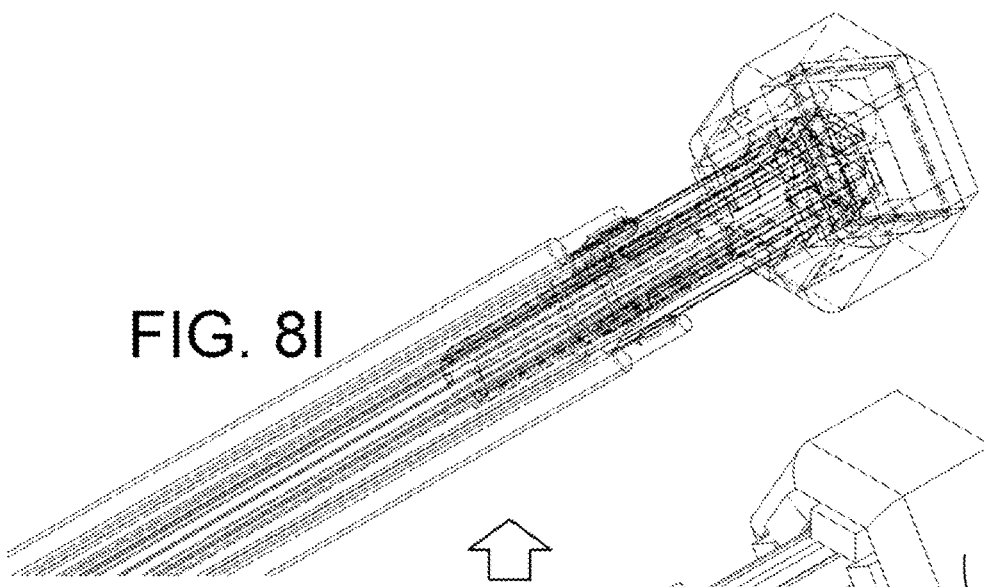
Figure 8H:
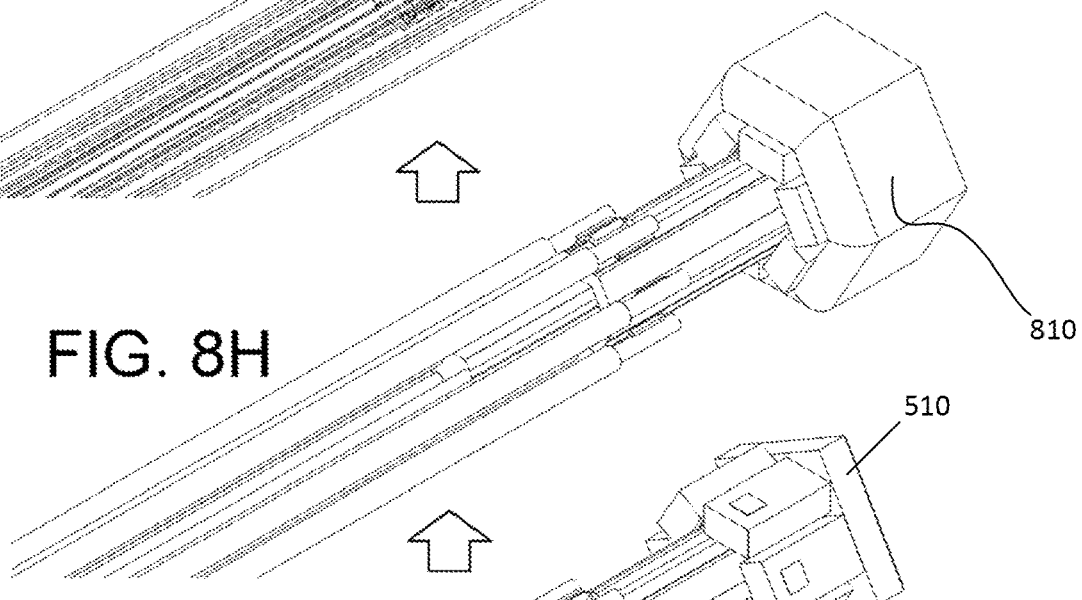
Figure 8G:
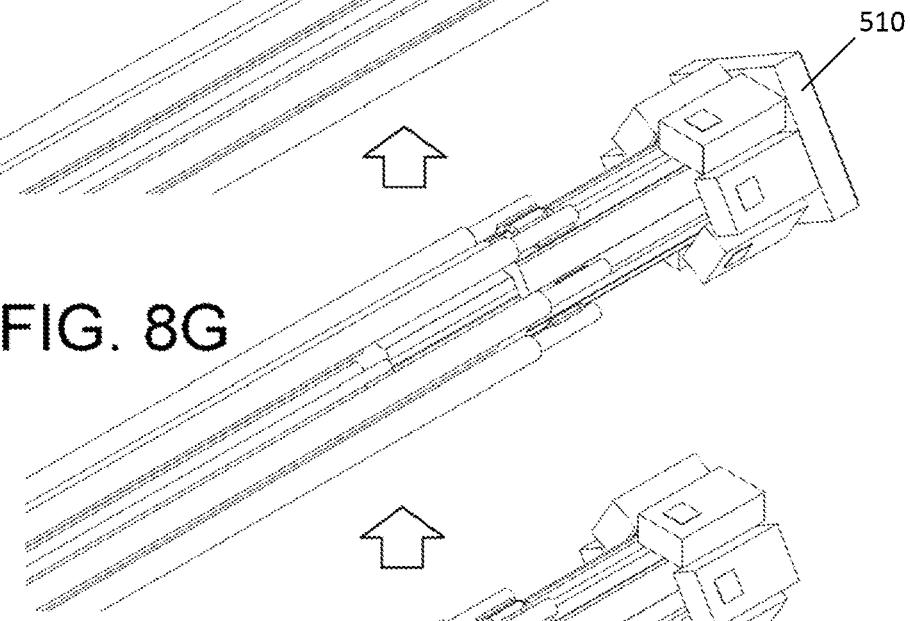
Figure 8F:
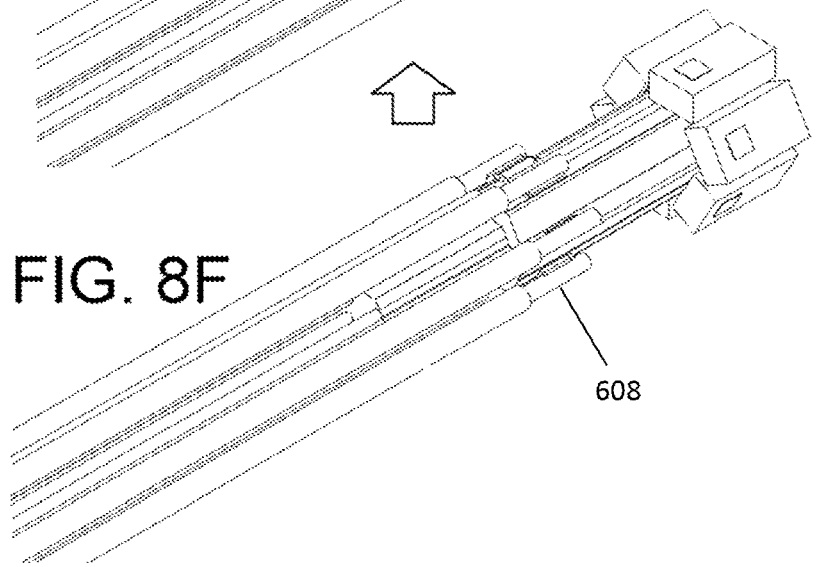

FIGS. 8A through 8I illustrate a sequence of the process of assembly of an embodiment of the RISC of the surgical scope. In this embodiment, the ring lens has a hexagonal cross-section building-up/constructing the RISC assembly. Specifically, FIGS. 8A, 8B, 8C, 8D, 8E, 8F, 8G, 8H, and 8I through 8I how a layer-by-layer arrangement of a ring illuminated surgical camera starting from the camera contact post 604 in FIG. 8A. Then, as shown in FIG. 8B, camera leads 617 are operably juxtaposed with the camera post 604, after which the LED support 201 is incorporated over the camera post 604, FIG. 8C. (The post 604 is dimensioned to fit into the longitudinal bore in the LED support 201, with a mechanical tolerance of about 0.05 mm, for example. The bore and the camera post have outer perimeters/cross-sections that may be geometrically similar in shape as the outer perimeter of the LED support 201, e.g. circular, square, pentagonal, or hexagonal.) Next, FIGS. 8D and 8E schematically depict the affixation of individual LED sources 205 to the LED support 201. The electrical incorporation/deposition of the camera conductors 608 to the LED leads 206, 206A of the LED support 201 is shown at the step of FIG. 8F. In FIG. 8G, the electronic imaging sensor (camera array) 510 is shown affixed and in relation to the LED sources 205. FIG. 8H now illustrates the ring lens 810 (a hexagonal ring lens 810, in the case of this specific implementation) pulled over the camera array 510 to at least partially enclose/be wrapped about the LED sources 205 and electronic imaging sensor 510. Finally, FIG. 8I schematically illustrates, in a transparent orthogonal view, the end of the surgical endoscope (without the endoscope sheath or cannula) equipped with the ring-illuminated surgical camera structured according to an idea of the invention.

Notably, the assembly of the ring-illuminated surgical camera can generally follow the order shown in FIGS. 8A through 8I or, alternatively, the assembly process can be modified depending on availability of the specific means of assembly. In one specific case, for example, the electronic imaging sensor 510 can be incorporated in the assembly after the ring lens of the embodiment is installed. In another related case, the electrical members (leads) can be cooperated with the embodiment after the assembly of the LED support, LED sources, camera post, and the ring lens has been substantially completed.

Figures 11A, 11B, 11C:
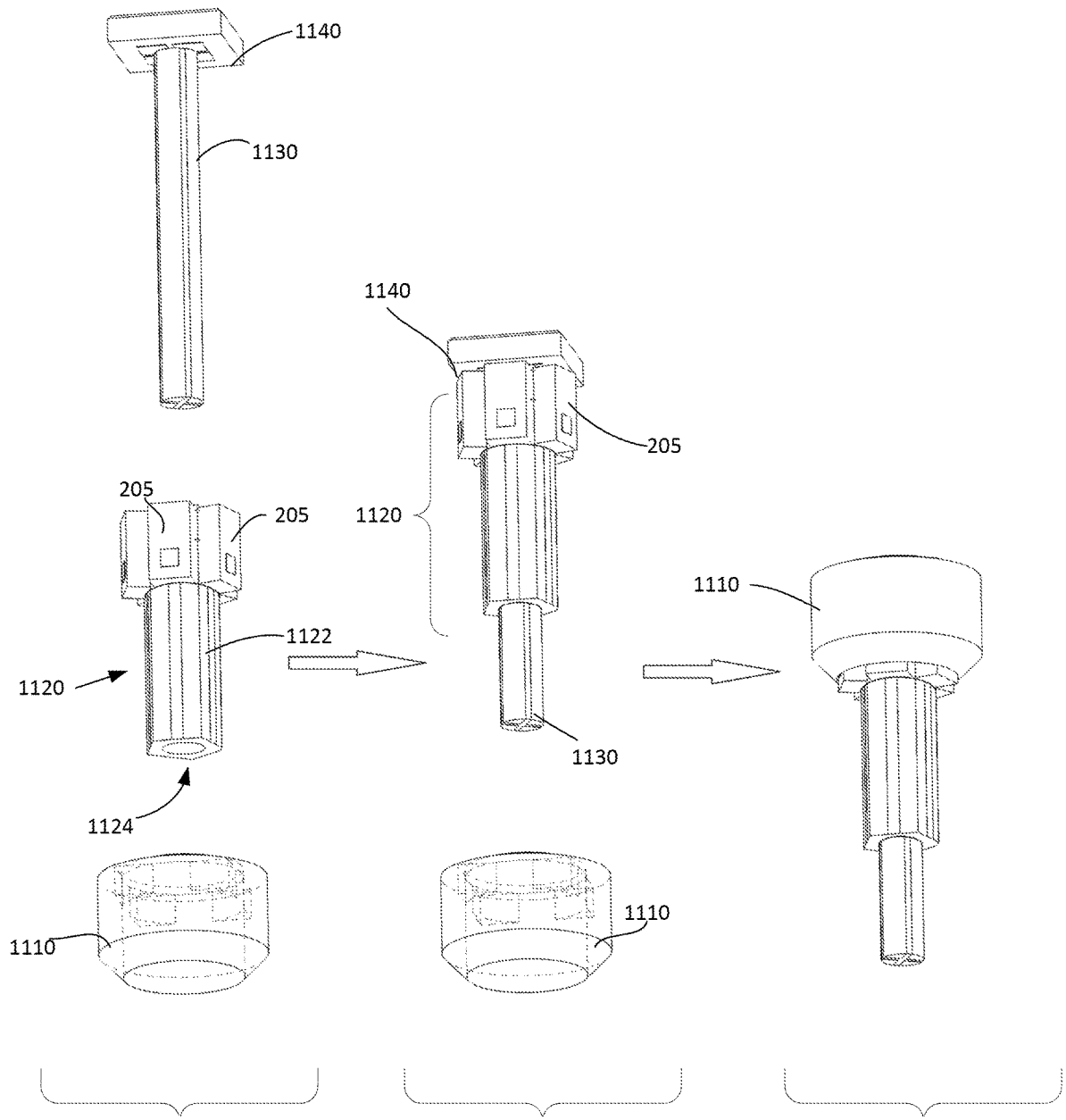
FIG. 11 (with sub-FIGS. 11A, 11B, 11C) illustrates schematically several components of an assembly of a ring-illuminated surgical camera, including the placement of the camera on the camera contact post, the LED support carrying the LEDs, and the ring lens.

FIG. 11 (with sub-FIGS. 11A, 11B, and 11C) schematically illustrates a related implementation of the process of assembly of the ring-illuminated camera of an embodiment of the surgical scope of the invention. Here, FIG. 11A shows, in an exploded view, the constituent components of the camera assembly: the ring-lens 1110 with the circular-cylindrical outer surface and the generally-rectangular counterbore in its distal portion (shown in dashed lines), the combination 1120 of the LED support 1122 with the axial bore 1124 and carrying LED sources 205 attached to the support 1122, and the camera post 1130 carrying the rectangularly-shaped electronic imaging sensor 1140. As shown in FIG. 11B, the post 1130 is inserted into the bore 1124 of the combination 1120 such that the LED sources 205 are placed in immediate proximity of the imaging sensor 1140. After such operational accommodation, and as shown in FIG. 11C, the ring-lens 1110 is appropriately positioned and affixed over the LED sources 205 and the sensor 1140, with the sensor rested in the rectangular counterbore nest of the ring-lens 1110.

An embodiment of a surgical scope, configured according to the idea of the invention, includes an illumination system including an embodiment of a ring-illuminated surgical camera (with a ring-lens) disposed in the tip of the scope as discussed herein, an endoscopic sheath or cannula affixed to an endoscopic tip, and a plurality of guidewires drawn to change the orientation of the endoscopic tip in operation of the scope. The ring illuminated surgical camera includes a ring lens that having an emission surface, a reflecting surface, and an external surface, a lumen defined by an internal surface that extends longitudinally from the emissions face to the reflector, and an electric wire conduit port passing through the emissions face and adapted to carry an electronic imaging sensor and imaging sensor electrical contacts. The camera additionally contains a plurality of light emitting diodes carried within the lumen, adjacent to the internal surface of the ring lens, and adapted to emit light radially with respect to the longitudinal axis of the ring lens; an electronic imaging sensor adjacent to the emission surface, the electronic imaging sensor having an imaging array and imaging sensor electrical contacts; and a plurality of imaging sensor electrical contacts in electrical contact with the electronic imaging sensor passing through the electric wire conduit port and through the ring lens. The endoscopic tip can further include at least one working channel adapted to provide instrument access and/or fluid flow to a surgical site, preferably, where the working channel passes through the emissions face.

Understandably, details of specific implementations of contents of the surgical scope may vary depending on the specific operational need.

FIG. 9 (with sub-FIGS. 9A, 9B, 9C, 9D, 9E, and 9F) schematically illustrates a related embodiment 976 of a ring lens of the endoscope, configured as one contiguous (single, non-separable) piece or unit or element. The lens 976 is preferably made from transparent polymeric or glass-based material (in which case it can be molded), or alternatively from quartz-based material (in which case it can be appropriates carved and polished), and serves more operation functions than the above-described embodiments of the ring lens. In particular, the lens 976 is configured to simultaneously perform the function of housing element in which auxiliary optics and/or components of the overall surgical camera can be at least partially enclosed. To this end, as shown, the essentially cylindrical element 976 has a chamfer 978 (or, alternatively, a geometrically-stepped profile) that extends as a substantially conical surface along at least part of the circumference of the proximal edge of the lens 976. The proximal edge of the lens 976 is dimensioned to match and/or mate a catheter tubing. The chamfer 978 is dimensioned to provide for the TIR of light propagating through the body of the lens 976 and/or is coated with the reflective material. Light-reflecting surfaces (reflectors) 980 are disposed at the outer diameter of the cylindrical body of the element 976. The ring-lens element 976 additionally includes a working channel port 982 that is counterbored, 984, from the opposite end of the element 976 to receive a working channel liner (not shown) and an image sensor chip (not shown). The element 976 also contains a recess 986 with an electric wire conduit port 988 that is counterbored, 990, for conduit attachment (not shown). The proximal side of the one-piece housing-and-lens element 976 contains a hollow 992 to provide space for staking LED sources 205 (not shown) facing radially outward or at skew angles within the structural voids of the hollow 992. The deflection control wires would be made to terminate within the metal ring (not shown) that mates to the chamfer 978 or the stepped outer profile. FIG. 9 depicts the case in which multiple reflectors or reflecting surfaces 980 are structured in a radial plane of the lens element 976 and positioned longitudinally about the ring lens to be spaced along the longitudinal axis of the lens 976 (visible as reflector surfaces 980A, 980B in FIG. 9B). In the specific case illustrated in FIGS. 9A-9F, the ring lens 976 can include four reflectors 980 positioned in two radial plane separated longitudinally along the axis of the ring lens.

The schematic illustrations of FIG. 10 (with sub-FIGS. 10A, 10B, 10C, 10D, 10E, and 10F) builds upon those of FIG. 9. Here, the embodiment 976 is shown complemented with LED sources 1010, disposed peripherally along the internal surface of the hollow (void) 992 across from the chamfered surface 978 with the LED emitters of the sources 1010 pointing radially outwards such as to deliver light output, in operation, towards the surface 978. At the same time, the element 976 contains additional LED sources 1010 disposed at levels of surfaces 980, which are additionally equipped with light-dispersing elements 1012.

As a result of having the layers of LED sources 1010 stacked along the axis of the element 976, light from some LED sources 1010 is directed to the chamfered surface 978 while light from LED sources 1010 disposed on a different level is directed towards the light-dispersing elements 1012. Uniformity of illumination may be further controlled by adding off radial mounting within the available space 992 and/or forming light-divergence-altering lens elements on the LED sources 1010.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

Within this specification, embodiments have been described in a way that enables a clear and concise specification to be written, but it is intended and will be appreciated that embodiments may be variously combined or separated without parting from the scope of the invention. In particular, it will be appreciated that each of the features described herein is applicable to most if not all aspects of the invention.

In addition, when the present disclosure describes features of the invention with reference to corresponding drawings (in which like numbers represent the same or similar elements, wherever possible), the depicted structural elements are generally not to scale, for purposes of emphasis and understanding. It is to be understood that no single drawing is intended to support a complete description of all features of the invention. In other words, a given drawing is generally descriptive of only some, and not necessarily all, features of the invention. A given drawing and an associated portion of the disclosure containing a description referencing such drawing do not, generally, contain all elements of a particular view or all features that can be presented is this view, at least for purposes of simplifying the given drawing and discussion, and directing the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. The described single features, structures, or characteristics of the invention may be combined in any suitable manner in one or more further embodiments.

For the purposes of this disclosure and the appended claims, the use of the terms "substantially", "approximately", "about" and similar terms in reference to a descriptor of a value, element, property, or characteristic at hand is intended to emphasize that the value, element, property, or characteristic referred to, while not necessarily being exactly as stated, would nevertheless be considered, for practical purposes, as stated by a person of skill in the art. These terms, as applied to a specified characteristic or quality descriptor means "mostly", "mainly", "considerably", "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

The invention as recited in claims appended to this disclosure is intended to be assessed in light of the disclosure as a whole, including features disclosed in related art to which reference is made.

The invention claimed is:

1. A multi-spectrum ring illuminated surgical endoscope comprising:
an endoscopic tip including a multi-spectrum ring illuminated camera, the multi-spectrum ring illuminated camera containing:
a ring lens having a reflector at a proximal end thereof, an emission surface at a distal end thereof, and a longitudinal axis running from the proximal end to the distal end;
a plurality of light-emitting diodes (LEDs) that are adjacent to an internal surface of the ring lens and configured to have light, generated by an LED from said plurality of LEDs, radially transmitted into the ring lens,
wherein the reflector is oriented to reflect the light, which has been transmitted radially into the ring lens, along the longitudinal axis,
wherein the plurality of LEDs includes at least one LED configured to emit a portion of said light at a plurality of wavelengths including between three and twelve different wavelengths;

an endoscopic cannula affixed to the endoscopic tip;

a plurality of guidewires positioned inside the cannula and connected with the endoscopic tip to vary an orientation of the endoscopic tip; and an array contact post extending in the endoscopic cannula along the longitudinal axis through the ring lens;

wherein the multi-spectrum ring illuminated camera further includes a grey-scale image capture sensor recessed into the ring lens and in electrical contact with the array contact post.

2. A multi-spectrum ring illuminated surgical scope according to claim 1, wherein the endoscopic tip further includes at least one working channel longitudinally extended therethrough and dimensioned to accommodate therein at least one of an instrument access and a flow of fluid from the endoscopic cannula to a surface of the endoscopic tip.

3. A multi-spectrum ring illuminated surgical scope according to claim 2, wherein at least one of the at least one working channel and the ring lens is asymmetric about a center of a proximal surface of the tip.

4. A multi-spectrum ring illuminated surgical scope according to claim 1, wherein the ring lens is configured as a unitary piece with the proximal end facing the endoscopic cannula.

5. A multi-spectrum ring illuminated surgical scope according to claim 1, wherein the grey-scale image capture sensor is configured to be adjacent to the emission surface, to be substantially transverse to the longitudinal axis, and to face an ambient medium.

6. A multi-spectrum ring illuminated surgical scope according to claim 1, wherein at least one of the following conditions is satisfied:
   a) wherein the plurality of LEDs includes at least two LEDs configured to emit light at each of three to twelve different wavelengths;
   b) wherein the plurality of LEDs includes at least one white-light LED; and
   c) wherein the plurality of LEDs includes multiple single-color LEDs, a color of light emitted by a first single-color LED in operation being different from a color of light emitted by a second single-color LED.

7. A multi-spectrum ring illuminated surgical scope according to claim 1, further comprising a support post with longitudinal hollow therein extending throughout the support post, and wherein the array contact post passes through said longitudinal hollow and carries electrical contact members within the longitudinal hollow, said electrical contact members connected to the grey-scale image capture sensor.

8. A multi-spectrum ring illuminated surgical scope according to claim 7, wherein the support post has multiple outer longitudinal facets extended along the longitudinal axis and a polygonal outer cross-section defined across the longitudinal axis, each of the outer longitudinal facets carrying a corresponding LED from the plurality of LEDs.

9. A multi-spectrum ring illuminated surgical scope according to claim 1, wherein a portion of the emission surface is configured to be exposed to an ambient medium.

10. A multi-spectrum ring illuminated surgical scope according to claim 1, comprising an optical window covering and fluidly sealing the grey-scale image capture sensor in a recess of the ring lens.

11. A multi-spectrum ring illuminated surgical scope according to claim 1, wherein at least one of the following conditions is satisfied:
   a) the ring lens has at least one of a polygonal outer perimeter and a polygonal inner perimeter as seen in a cross-section of the ring lens that is defined in a plane transverse to the longitudinal axis;
   b) the reflector includes a substantially conical surface;
   c) the emission surface is a substantially planar surface transverse to the longitudinal axis;
   d) the endoscopic cannula includes a metallic tubular member; and
   e) at least one of the reflector and an external surface of the ring lens carries a reflective coating thereon.

12. A multi-spectrum ring illuminated surgical scope according to claim 1, wherein the ring lens includes a void adjacent to the proximal end thereof.

13. A multi-spectrum ring illuminated surgical scope according to claim 1, wherein an LED source from the plurality of LED sources is equipped with an LED-radiation-shaping lens carried thereon and at least partially covering a facet of an LED emitter of said LED source.

14. A multi-spectrum ring illuminated surgical scope according to claim 13, wherein the LED-radiation-shaping lens has an external surface that is substantially congruent with an internal surface of the ring lens.

15. A multi-spectrum ring illuminated surgical scope according to claim 1,
   wherein an LED source from the plurality of LED sources is equipped with an LED-radiation-shaping lens carried thereon,
   wherein the LED-radiation-shaping lens has a semi-cylindrical surface with a curvature matching a curvature of an internal surface of the ring lens or wherein the LED-radiation-shaping lens has a plurality of flat surfaces that are substantially geometrically matched to a plurality of flat internal surfaces of the ring lens.

16. A multi-spectrum ring illuminated surgical scope according to claim 1, wherein the reflector is inclined with respect to an internal surface of the ring lens to substantially totally internally reflect light incident thereon from a corresponding LED of the plurality of the LEDs.

* * * * *